United States Patent
Radziemski et al.

(10) Patent No.: US 8,974,366 B1
(45) Date of Patent: Mar. 10, 2015

(54) HIGH POWER ULTRASOUND WIRELESS TRANSCUTANEOUS ENERGY TRANSFER (US-TET) SOURCE

(71) Applicant: Piezo Energy Technologies, LLC, Tucson, AZ (US)

(72) Inventors: Leon J. Radziemski, Tucson, AZ (US); Inder Raj Singh Makin, Tucson, AZ (US)

(73) Assignee: Piezo Energy Technologies, LLC, Tucson, AZ (US)

(*) Notice: Subject to any disclaimer, the term of this patent is extended or adjusted under 35 U.S.C. 154(b) by 0 days.

(21) Appl. No.: 14/475,295

(22) Filed: Sep. 2, 2014

Related U.S. Application Data

(63) Continuation-in-part of application No. 13/734,817, filed on Jan. 4, 2013, now abandoned.

(60) Provisional application No. 61/585,101, filed on Jan. 10, 2012.

(51) Int. Cl.
*A61N 1/378* (2006.01)
*A61M 1/12* (2006.01)
*A61M 1/10* (2006.01)

(52) U.S. Cl.
CPC ............ *A61M 1/127* (2013.01); *A61M 1/1086* (2013.01)
USPC .............................................. 600/16; 607/61

(58) Field of Classification Search
CPC . A61N 1/37217; A61N 1/37235; H02J 17/00; A61M 1/127; A61M 2205/8237
USPC .................................. 607/33, 61; 600/16–17
See application file for complete search history.

(56) References Cited

U.S. PATENT DOCUMENTS

| | | | |
|---|---|---|---|
| 4,160,234 | A | 7/1979 | Karbo et al. |
| 4,748,366 | A | 5/1988 | Taylor |
| 4,748,985 | A | 6/1988 | Nagasaki |
| 5,237,239 | A | 8/1993 | Inoue et al. |

(Continued)

FOREIGN PATENT DOCUMENTS

| | | |
|---|---|---|
| CA | 23799427 | 8/1999 |
| CA | 2 364 853 | 9/2000 |

(Continued)

OTHER PUBLICATIONS

JS. Yang et al., "Extensional vibration of a nonuniform piezoceramic rod and high voltage generation", International Journal of Applied Electromagnetics and Mechanics IOS Press, 2000, 7 pages.

(Continued)

*Primary Examiner* — Mark W Bockelman
(74) *Attorney, Agent, or Firm* — Hayes Soloway P.C.

(57) ABSTRACT

A bio-implantable energy capture and storage assembly is provided. The assembly includes an acoustic energy transmitter and an acoustic energy receiver. The acoustic energy receiver also functions as an energy converter for converting acoustic energy to electrical energy. An electrical energy storage device is connected to the energy converter, and is contained within a bio-compatible implant for implantation into tissue. The acoustic energy transmitter is separate from the implant, and comprises a substantially 2-dimensional array of transmitters. The acoustic energy converter may also provide conditioned power directly to a load, connected to said energy converter.

20 Claims, 14 Drawing Sheets

(56) References Cited

U.S. PATENT DOCUMENTS

| | | | |
|---|---|---|---|
| 5,239,518 A | 8/1993 | Kazmar | |
| 5,300,875 A | 4/1994 | Tuttle | |
| 5,320,104 A | 6/1994 | Fearnside et al. | 128/661.01 |
| 5,376,857 A | 12/1994 | Takeuchi et al. | |
| 5,411,537 A | 5/1995 | Munshi et al. | |
| 5,494,468 A | 2/1996 | Demarco, Jr. | |
| 5,501,222 A | 3/1996 | Briggs | |
| 5,545,942 A | 8/1996 | Jaster et al. | |
| 5,555,887 A | 9/1996 | Fraser et al. | |
| 5,560,362 A | 10/1996 | Sliwa, Jr. et al. | |
| 5,585,546 A | 12/1996 | Gururaja et al. | |
| 5,629,599 A | 5/1997 | Malaspina et al. | |
| 5,629,678 A | 5/1997 | Gargano et al. | |
| 5,630,836 A | 5/1997 | Prem et al. | |
| 5,671,746 A | 9/1997 | Dreschel et al. | |
| 5,703,474 A | 12/1997 | Smalser | |
| 5,749,909 A | 5/1998 | Schroeppel et al. | |
| 5,751,091 A | 5/1998 | Takahashi et al. | |
| 5,788,453 A | 8/1998 | Donde et al. | |
| 5,810,015 A | 9/1998 | Flaherty | |
| 5,835,996 A | 11/1998 | Hashimoto et al. | |
| 5,889,383 A | 3/1999 | Teich | |
| 5,918,502 A | 7/1999 | Bishop | |
| 5,925,972 A | 7/1999 | Shrader et al. | |
| 5,961,465 A | 10/1999 | Kelly, Jr. et al. | |
| 5,998,910 A | 12/1999 | Park et al. | |
| 6,185,452 B1 | 2/2001 | Schulman et al. | |
| 6,196,932 B1 | 3/2001 | Marsh et al. | |
| 6,201,336 B1 | 3/2001 | Burns | |
| 6,215,733 B1 | 4/2001 | Rynne et al. | |
| 6,224,493 B1 | 5/2001 | Lee et al. | |
| 6,342,776 B1 | 1/2002 | Taylor et al. | |
| 6,407,484 B1 | 6/2002 | Oliver et al. | |
| 6,424,079 B1 | 7/2002 | Carroll | |
| 6,432,050 B1 | 8/2002 | Porat et al. | |
| 6,433,465 B1 | 8/2002 | McKnight et al. | |
| 6,475,170 B1 | 11/2002 | Doron et al. | |
| 6,579,315 B1 | 6/2003 | Weiss | |
| 6,654,638 B1 | 11/2003 | Sweeney | |
| 6,720,709 B2 | 4/2004 | Porat et al. | |
| 6,737,789 B2 | 5/2004 | Radziemski et al. | |
| 6,764,446 B2 | 7/2004 | Wolinsky et al. | |
| 6,798,716 B1 | 9/2004 | Charych | |
| 7,003,353 B1 | 2/2006 | Parkhouse | |
| 7,024,248 B2 | 4/2006 | Penner et al. | |
| 7,198,603 B2 | 4/2007 | Penner et al. | 600/486 |
| 7,283,874 B2 | 10/2007 | Penner | |
| 7,314,447 B2 | 1/2008 | Park et al. | |
| 7,489,967 B2 | 2/2009 | Von Arx et al. | |
| 7,505,816 B2 | 3/2009 | Schmeling et al. | |
| 8,082,041 B1 | 12/2011 | Radziemski | |
| 8,364,276 B2 | 1/2013 | Willis | 607/61 |
| 2001/0032663 A1 | 10/2001 | Pelrine et al. | |
| 2001/0035723 A1 | 11/2001 | Pelrine et al. | |
| 2003/0137221 A1 | 7/2003 | Radziemski et al. | |
| 2004/0002655 A1 | 1/2004 | Bolorforosh et al. | |
| 2004/0172083 A1 | 9/2004 | Penner | |
| 2005/0033316 A1 | 2/2005 | Kertz | |
| 2005/0075696 A1 | 4/2005 | Forsberg et al. | |
| 2005/0187594 A1 | 8/2005 | Hatlestad | |
| 2005/0256549 A1 | 11/2005 | Holzer | |
| 2005/0288739 A1 | 12/2005 | Hassler, Jr. et al. | |
| 2006/0009818 A1 | 1/2006 | Von Arx et al. | |
| 2006/0136005 A1 | 6/2006 | Brisken et al. | |
| 2006/0247738 A1 | 11/2006 | Schmeling et al. | |
| 2007/0093875 A1 | 4/2007 | Chavan et al. | |
| 2008/0021510 A1 | 1/2008 | Mi et al. | |
| 2008/0108915 A1 | 5/2008 | Penner | |
| 2008/0188755 A1 | 8/2008 | Hart | |
| 2008/0294208 A1 | 11/2008 | Willis et al. | 607/3 |
| 2008/0312720 A1 | 12/2008 | Tran et al. | |
| 2009/0259273 A1 | 10/2009 | Figueiredo et al. | 607/32 |
| 2010/0234924 A1 | 9/2010 | Willis | 607/63 |

FOREIGN PATENT DOCUMENTS

| | | |
|---|---|---|
| EP | 1 666 087 | 2/1998 |
| EP | 1 162 922 | 9/2000 |
| FR | 2616335 | 12/1988 |
| JP | 2000-350708 | 12/2000 |
| WO | 99/51303 | 10/1999 |
| WO | WO 00/56241 | 9/2000 |
| WO | 2006/010010 | 1/2006 |
| WO | WO2006/119098 | 11/2006 |
| WO | WO 2008/156981 | 12/2008 |

OTHER PUBLICATIONS

Park et al, "Crystal Growth and Ferroelectric Related. Properties of $(1-x) Pb(A_{1/3} Nb_{2/3})O_3 -x PbTiO_3 (A=Zn^{2+}, Mg^{2+})$", IEEE, 1996, pp. 79-82.

"Material properties of PZN-8% PT Single Crystal", PennState, 1 page.

"Material properties of PMN-33% PT Single Crystal", PennState, 1 page.

US. Official Action (mail) dated Jun. 25, 2009 (13 pgs).

Hideyuki Kawanabe, et al. "Power and Information Transmission to Implanted Medical Device Using Ultrasonic", The Japan Society of Applied Physics, vol. 40 (2001), pp. 3865-3866.

Suzuki et al., "Fundamental Study of an electric power transmission system for implanted medical devices using magnetic solar energy", The Japanese Society for Artificial Organs, 2003, pp. 145-148.

Hu, et al. "Transmitting Electric Energy Through a Metal Wall by Acoustic Waves Using Piezoelectric Transducers", IEEE vol. 50, No. 7, Jul. 2003, pp. 773-781.

"Smart Materials Transducers as Power Sources for MEMs Devices", Int. Symp. On Smart Structures and Microsys, Clark et al., 2000.

"Comprehensive compilation of empirical ultrasonic properties of mammalian tissues", Goss et al., J. Acoust. Soc. Am. 64, pp. 423-457, 1978.

"Trends in Cardiac Pacemaker Batteries", Mallela et al., Indian Pacing and Electrophysiology J. 4, pp. 201-212, 2004.

"The future of lithium-ion batteries in implantable medical devices", Schmidt et al., J. of Power Sources 97-98, pp. 742-746, 2001.

"Stimulating and Sensing Network Inside the Human Body", Schulman, Proc. Int. Workshop on Wearable Computing BSN '06, 0-7695-2547-4/06 IEEE, 2006.

"Growth and characterization of single-crystal lead magnesium niobate-lead titanate via high-pressure vertical Bridgman method", Soundararajan et al., J. of Mat. Res., 19(2), pp. 609-615, 2004.

USFDA Information for Manufacturers Seeking Marketing Clearance of Diagnostic Ultrasound Systems and Transducers, Center for Devices and Radiological Health, U.S. Food and Drug Administration, Rockville, MD, 1997.

"Elastic, piezoelectric, ad dielectric properties of multidomain $0.67Pb(Mg_{1/3} Nb_{2/3}) O_3 —0.33PbTiO_3$ single crystals", J. Appl. Physics, 90, pp. 3471-3476, 2001.

NCRP Report No. 140, Recommendations of the National Council on Radiation Protection and Measurements, "Exposure Criteria for Medical Diagnostic Ultrasound: II. Criteria Based on all Known Mechanisms," Dec. 31, 2002 , pp. 284-289 (4 pgs).

Danilov et al., "Progress in Methods for Transcutaneous Wireless Energy Supply to Implanted Ventricular Assist Devices," Biomedical Engineering, vol. 44, No. 4, 2010, pp. 125-129 (5 pgs).

Fuller et al., "Real Time Imaging with the Sonic Window: A Pocket-Sized, C-Scan, Medical Ultrasound Device," 2009 IEEE International Ultrasonics Symposium Proceedings, pp. 196-199 (4 pgs).

Hedrick, W., "A Guide to Clinical Safety," Journal of Diagnostic Medical Sonography, Nov./Dec. 2005, vol. 21, No. 6, pp. 455-461 (8 pgs).

Lawry et al., "Electrical optimization of power delivery through thick steel barriers using piezoelectric transducers," Proc. of SPIE, vol. 7683 (12 pgs).

Mehta et al., "The LionHeart LVD-2000: A Completely Implanted Left Ventricular Assist Device for Chronic Circulatory Support," Ann Thorac Surg, 2001, vol. 71, pp. S156-S1561 (6 pgs).

(56) References Cited

OTHER PUBLICATIONS

NCRP Report No. 113, Recommendations of the National Council on Radiation Protection and Measurements, "Exposure Criteria for Medical Diagnostic Ultrasound: I. Criteria Based on Thermal Mechanisms," Jun. 1, 1992, pp. 52-53 (2 pgs).

Ranganathan et al., "Direct Sampled I/Q Beamforming for Compact and Very Low-Cost Ultrasound Imaging," IEEE Transactions on Ultrasonics, Ferroelectrics, and Frequency Control, Sep. 2004, vol. 51, No. 9, pp. 1082-1094 (13 pgs).

Schuder, J., "Powering an Artificial Heart: Birth of the Inductively Coupled-Radio Frequency System in 1960," Artificial Organs, 2002, vol. 26, No. 11, pp. 909-915 (7 pgs).

Slaughter et al., "Transcutaneous Energy Transmission for Mechanical Circulatory Support Systems: History, Current Status, and Future Prospects," J Card Surg, 2010, vol. 25, pp. 484-489 (7 pgs).

Suzuki et al., "Fundamental study of an electric power transmission system for implanted medical devices using magnetic and ultrasonic energy," J Artif Organs, 2003, vol. 6, pp. 145-148 (4 pgs).

Woodcock, J.P., "Ultrasonics," Medical Physics Handbooks 1, Adam Hilger Ltd., Bristol in collaboration with the Hospital Physicists' Association, pp. 6-7 (2 pgs).

Si et al., "A Frequency Control Method for Regulating Wireless Power to Implantable Devices," IEEE Transactions on Biomedical Circuits and Systems, Mar. 2008, vol. 2, No. 1, pp. 22-29 (8 pgs).

Kang et al., "Closed Loop Liquid Cooling for High Performance Computer Systems," Proceedings of IPACK2007, ASME InterPAK '07, Jul. 8-12, 2007, Vancouver, British Columbia, Canada (7 pgs).

Franco et al., "Advanced Therapy in Cardiac Surgery," PMPH USA, Second Edition, Apr. 2003 (book description only).

PCT International Search Report and the Written Opinion issued in corresponding application No. PCT/US2013/020577, dated Mar. 11, 2013 (9 pgs).

PCT Notification Concerning Transmittal of International Preliminary Report on Patentability issued in corresponding application No. PCT/US2013/020577, dated Jul. 24, 2014 (7 pgs).

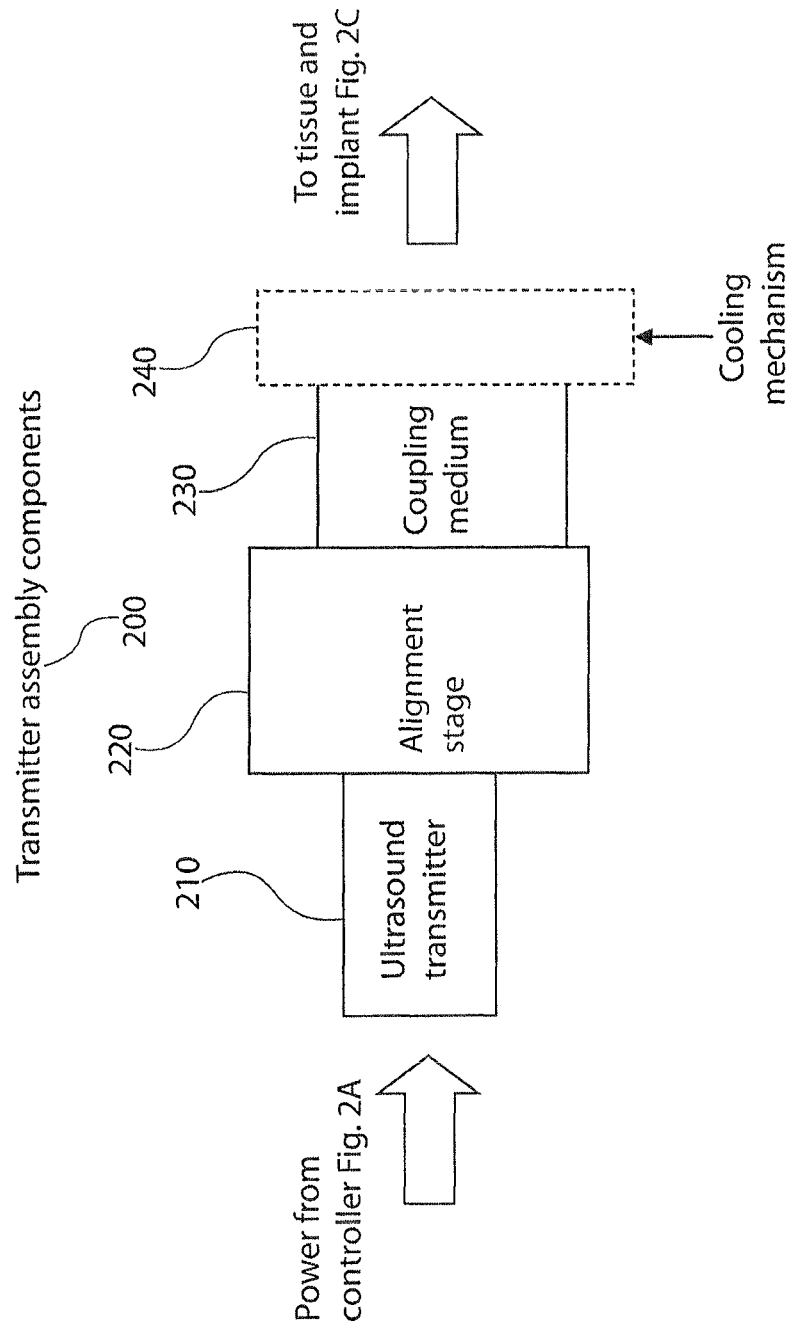

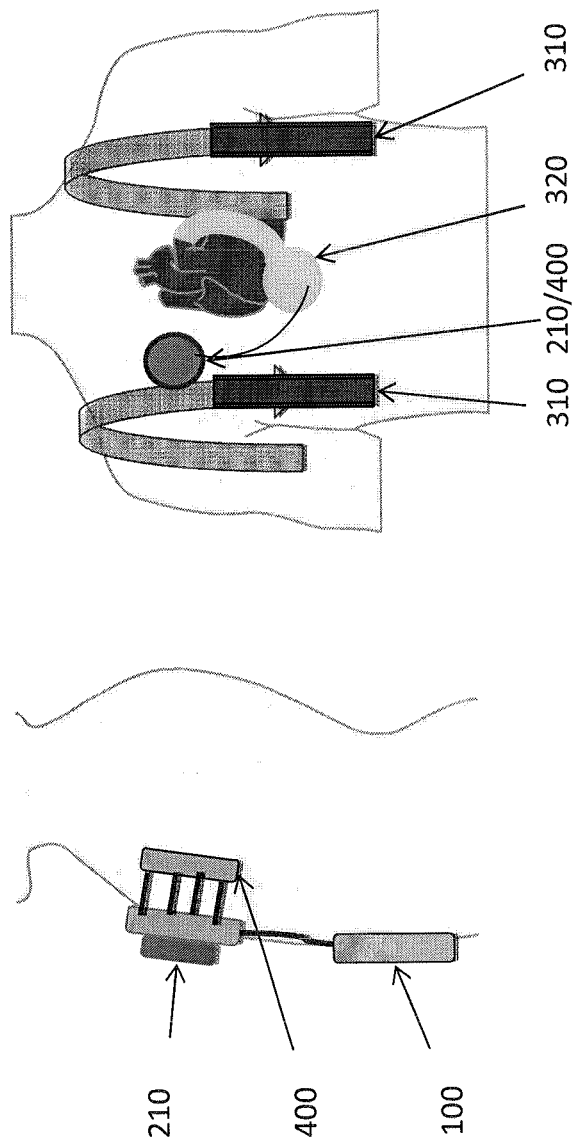

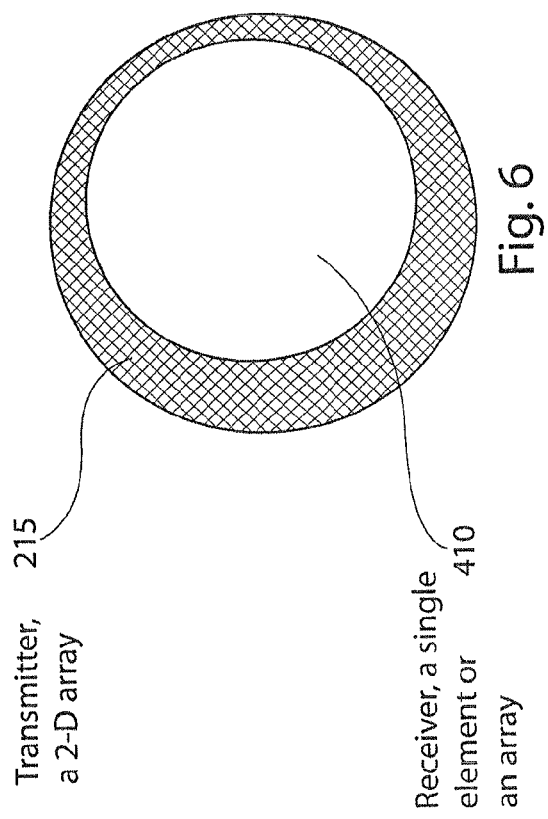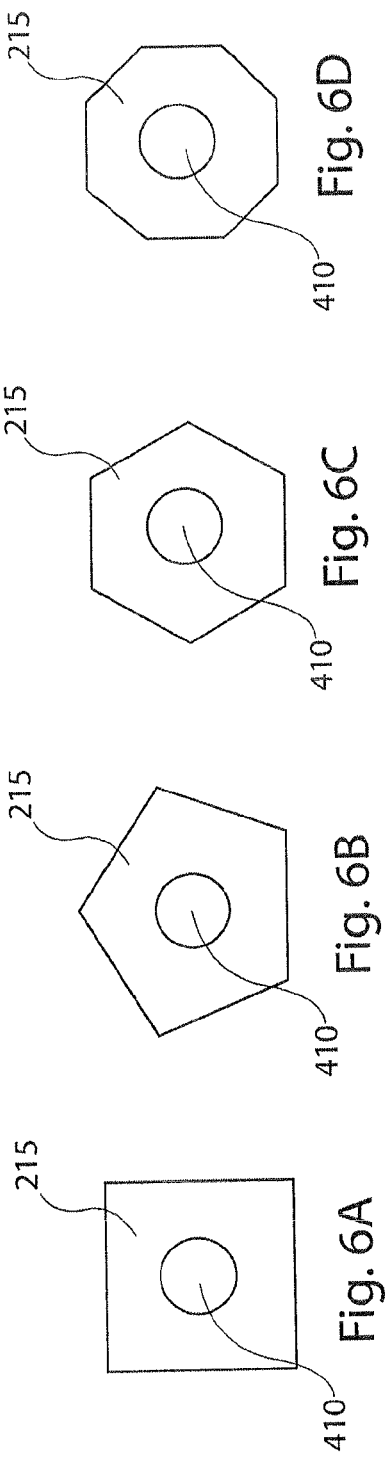

US 8,974,366 B1

HIGH POWER ULTRASOUND WIRELESS TRANSCUTANEOUS ENERGY TRANSFER (US-TET) SOURCE

CROSS REFERENCE TO RELATED APPLICATION

This application is a continuation-in-part of our co-pending U.S. application Ser. No. 13/734,817, filed Jan. 4, 2013, which application in turn claims priority from U.S. Provisional Application Ser. No. 61/585,101, filed Jan. 10, 2012, the contents of which are incorporated herein in their entireties.

STATEMENT REGARDING FEDERALLY SPONSORED RESEARCH OR DEVELOPMENT

This invention was made with Government support under grants number 1R43EB007421-01A1 and number R44EB007421 awarded by the National Institutes of health. The government has certain rights in the invention.

BACKGROUND OF THE INVENTION

The present invention relates to systems for powering implanted devices. The invention has particular utility for systems for powering current implanted devices requiring 24/7 operation and tens of watts of electrical power for applications such as heart-assist devices and will be described in connection with such utility, although other utilities are contemplated.

The present invention addresses a critical barrier to a major increase in the availability of heart assist-devices to patients in need: the present method of providing 24/7 continuous power to these devices, either as bridges to transplants or as permanent implants. Many publications cite the shortcomings of the existing method, which uses percutaneous links to provide electrical power to Mechanical Circulatory Support Systems (MCSS), for example, left- or right-Ventricular Assist Devices (VADs). These include Slaughter and Myers (2010), Si et al (2008), Danilov et al (2008), and Franco and Verrier (2003). The percutaneously placed wires provide pathways for infection (Franco and Verrier place the rate of infections at 40-45%), they periodically break, potentially create adhesions, and they limit the life style of patients because of measures they must take to avoid infections. A 2001 news release from NIH about the 1998-2001 REMATCH clinical study of percutaneously powered LVADs cited the probability of infection within 3 months of implantation to be 28%. As a result, at this time, the use of VADs is limited to bridge-to-transplant patients, those with extreme loss of heart capability.

Wireless Transcutaneous Energy Transfer (TET) across tissue is the much-preferred, less-invasive method of providing power to these devices. The impacts of a TET power system are that it 1) overcomes a major disadvantage of the present percutaneous method of providing power, namely high susceptibility to infection, opening up a lifesaving technology to hundreds of thousands who suffer from heart failure, and 2) supports the increased use of presently implanted heart-assist devices, and 3) fosters new devices targeted to improving human health.

Powering of MCSS over long periods of time solely by implanted batteries is not possible with the batteries available today because of the continuous high power requirement, which in turn dictates a large storage capacity and heavy battery. A TET system could deliver power directly to the application, while also charging an implanted battery which could take over for periods of 1 to 2 or a few hours. Over the past 50 years much effort has been expended in trying to make an electromagnetic method of TET (EM-TET) work for MCSS. U.S. Pat. No. 6,579,315, to Weiss discloses an EM-TET system for an artificial heart. U.S. Pat. No. 5,630,836 to Prem discloses an EM-TET system for both an artificial heart and a ventricular assist device. Papers (Mehta et al., 2001; Schuder, 2002; Slaughter and Myers, 2010; Danilov, 2010) disclose elements of an EM-TET system and even some clinical trials. Nevertheless only a few if any devices based on this principle are commercially realized. Issues that hold back EM-TET adoption include 1) heating of tissue due to misalignment of transmitter and receiver coils which expose metal to magnetic and electric fields that cause eddy-current heating, 2) heating due to losses in the coils, 3) loss of transmission efficiency with depth of penetration, due to decreased coupling of transmitter and receiver, and 4) decoupling due to perturbation of the inductance of the coils when they interact with nearby metallic or magnetic materials.

U.S. Pat. No. 8,082,041 (Radziemski) describes an ultrasound system suitable for providing low power to devices such as pacemakers, defibrillators and neurostimulators, primarily to recharge implanted batteries. It is well known in the art that batteries for such low power devices are charged for periods of minutes to hours at a rate of once per day to once per month or even less frequently. The patent also contains a description of the prior art with regard to medical-ultrasound power transmission, which is included by reference. These applications typically require a few Watts of input power and typically less than a half-Watt of power at the point of application and do not require addressing the new issues which must be resolved for high-power applications. Specifically the aforesaid patent teaches a bio-implantable energy capture and storage assembly, including an acoustic energy transmitter for contact with the skin, and an acoustic energy receiver converter for converting acoustic energy to electric energy; a battery or capacitor connected to the energy converter; signals upon which one may base alignment of transmitter and receiver; and a method of cooling the assembly. The acoustic energy receiver/converter, which employs ultrasound, is contained within a biocompatible implant.

Although methods for providing signals for alignment of transmitter and receiver are taught in Radziemski, the actual physical methods of aligning those elements is not taught. Absent any electronics to perform the alignment, the only option is that it would be performed manually, by physically adjusting the orientation of the external transmitter unit. In fact that is the present state-of-the-art method for the low power EM-TET method used commercially. In contrast, here is taught a 24/7 high-cooling-capacity element plus a 24/7 non-mechanical alignment system. Such an alignment system is required because solely manual alignment of transmitter and receiver over 24 hours of each day is wholly impractical and unsafe.

The cooling methods taught in Radziemski only included thermoelectric, disposable, or reusable coolers on the transmitter side, and phase change materials in the receiver. These would not be useful for the 24/7 continuous high-power operation needed for MCSS applications. This application requires one to two orders of magnitude more power than the applications discussed in Radziemski, typically at this time 10 Watts, or 20 Watts or more of electrical power at the device to be powered. This in turn, because of the finite efficiencies of all the steps, requires 40, 50, or 60 or more Watts of acoustic power from the transmitter unit. These levels of power require new and novel approaches for safely cooling tissue. Completely passive cooling methods alone, such as a disposable liquid coolant pack as taught in Radziemski, cannot dissipate the substantial 24/7 heat load generated in this high-power application, because such a pack would need to be changed and reapplied an undue number of times a day—making it wholly impractical. Phase change materials in the receiver implant cannot perform continuous cooling in that location because, once the transition has been made, they need time and lower temperatures to regain the previous phase. That time is not available in the 24/7 operation of a MCSS. A thermoelectric cooler as taught in Radziemski is also unusable in the present application because, as is well known in the art, it generates heat itself in proximity to itself and the skin which is dangerous to the patient and adds to the proximate heat load. Likewise cooling systems that operate in the transmitter, such as taught in Sliva (U.S. Pat. No. 5,560,362) do not apply here because those were single-ended systems used in imaging, with low heat loads and low cooling capabilities, and designed to operate pulsed with low duty cycles, not 24/7. They could cool the upper layer of the skin, but would not propagate deeply enough to cool a heat-source in the receiver and the tissue adjacent to it, as must be performed in the present application. Hence there exists a compelling need for an ultrasound delivery system that can deliver 10's of Watts of electrical power continuously while providing a) reliable non-mechanical alignment system, and 2) sufficient cooling capacity to dissipate potential tissue damage.

Although the present state of the art is to require 10 or more Watts to the MCSS, with efficiency improvements in the future, the requirements could be reduced to 5 Watts or less. Also MCSS placed in infants or young children may require less power as well. In those cases the demands on US-TET MCSS power delivery and heat removal will be correspondingly reduced, for example to 5 Watts and 3 Watts respectively.

The invention described here is a modality for transferring energy at a high rate (e.g. power) wirelessly and safely across the skin in quantities sufficient to directly power energy-intensive implantable medical devices.

There are few prior references to using ultrasound as a carrier of energy at the levels needed in heart assist devices. Suzuki, et al (2003) describe a hybrid magnetic-ultrasonic device that employs magnetostrictive materials to generate the pressure waves that carry energy across the skin. That paper mentions ultrasound, but refers to a different and more complex system that only demonstrated ~5 W of output power. High power ultrasound non-medical applications are well known in that field.

An important theoretical and practical advantage of US-TET is the ability to mitigate the effects of lateral and angular misalignment by non-mechanical electronic means via a two dimensional array of transmitter transducers, leading to a completely self-aligning system that does not require patient intervention. Also, the ultrasound beam, in the near field which is our case, does not diverge significantly, hence losses due to depth of the implant are minimal. Both of these advantages accrue to ultrasound because of its wave nature, and the fact that for power transfer, the ultrasound wavelength at useful frequencies is much smaller than the dimensions of the ultrasound transducers. In EM-TET the converse is true, ruling out the use of non-mechanical alignment by this principle. Willis (US2008/0294208) teaches the use of a two-dimensional ultrasound array to search for a receiver located in or on the heart and provide pacing level voltages to the heart wirelessly. Willis (U.S. Pat. No. 8,364,276) estimates the energy per pacing pulse provided as 0.17 microJoules in a 0.5 millisecond pulse. Assuming a pulse rate of 60 per second, this converts to an average power of 0.17 microWatts. TET-MCSS applications need on the order of 10-20 Watts continuously (10-20 Joules per second). Hence Willis' array without cooling could not be used in the present application. Also, in the MCSS application there is no need for a location function or signal. Willis is trying to find a small receiver some variable distance or orientation with respect to the transmitter array. In the MCSS application the plane transmitter and receiver faces will likely be 10 to 50 mm apart, and very closely parallel to begin with, their diameters being up to 75 mm or more, hence significantly larger than the distance separating them. An unfocused beam will suffice to correct any misalignment by changing the angle of the transmitted wave front so that it is incident upon the receiver closely parallel to the plane face of the receiver, thereby optimizing power delivery.

It is thus an object of the present invention to provide new and novel wireless power transfer techniques which alleviate distress, pain, complications, and operations associated with infections suffered by patients who would instead have to use the present method of power delivery to heart assist devices.

SUMMARY OF THE INVENTION

The present invention provides a new method and apparatus for powering an implanted device, such as a heart-assist device, and more particularly to an ultrasound wireless Transcutaneous Energy Transfer (US-TET) source generating 40, 50 or 60 or more Watts of acoustic power to operate an implanted device 24/7. In one aspect, an external transducer is connected to a battery-driven controller that modulates the power provided to the transmitter. In another aspect, the power may be supplied by other means, for example from an electrical power outlet fixed in a home or any other location. In another aspect, the power may be supplied intermittently by an internal battery which is kept charged during the continuous operation of the transmitter. In this latter case the internal battery takes over while the depleted external batteries are being replaced by completely charged ones, or for occasional bathing or other patient conveniences. The external controller will receive several radio frequency feedback signals wirelessly from the implant in order to regulate the transmitter power and frequency, to stabilize the power provided to the MCSS at an adequate level, and provide peak power as necessary.

Traditionally semi-solid ultrasound gels are introduced between the transducer face and the skin surface to attain adequate acoustic coupling between the transducer and tissue. This approach is limiting for the MCSS application since application of the semi-solid gel is untidy, and over the time of 24/7 operation the gel can dry. In a preferred embodiment, the transducer surface is coupled to the skin surface using newer direct—coupling means, such as a transducer face impregnated with silicone oils, vegetable oils, castor oil, or one of several other natural and synthetic media. The front face of the transducer is soft and forms a "boot" made out of an acoustic impedance matched thickness, using materials such as polyurethane, polyethylene glycol, polyethylene oxide, or other materials with acoustic impedance between that of the piezo-electric material and soft tissue.

At MCSS power levels, which are high for medical devices, a light-weight, active or active-passive combination cooling technique is necessary to keep the temperature of the patient's skin, intervening tissue, and tissue surrounding the implant within safe bounds. Well-developed off-the-shelf desktop computer CPU coolers have the capacity and are of size and weight to be useful as or models for the 24/7 coolers needed for MCSS. They typically have power requirements of 2-10 Watts, and so can be powered from the external batteries that are providing power to the ultrasound transmitter. The most suitable types are circulating liquid coolers and heat pipe coolers. They have low-profile round or square cooling pads that have a circulating working fluid and transport the heat away to an area where an air-cooled heat exchanger rejects the heat to ambient. The latter may be achieved passively through heat sinks or actively through radiator-fan assemblies. Liquid coolers come with flexible hoses and circulate a liquid working fluid while the heat pipes typically have rigid pipes and the working fluid undergoes a phase change in a closed-loop cycle for a highly efficient heat transport. These coolers can cope with desktop CPUs which generate between 30 W and 120 W, which as will be seen below, is more than adequate cooling for this application.

Temperature sensing devices within the transmitter and receiver relay temperatures to the external controller, which will then apply the correct power to the cooling device in order to keep the temperature of the transmitter, receiver, and intervening tissue at safe values. The piezoelectric elements which are the heart of the transmitter and receiver may geometrically be monolithic single elements, or a one- or two-dimensional array of small piezoelectric elements. Capacitively Machined Ultrasound Transducers (CMUTs), composite or polymer piezoelectric materials, or other mechanisms for inducing ultrasound vibrations are an alternative to conventional piezoelectric elements. In a preferred embodiment, a 2-dimensional array can be used to provide non-mechanical alignment of transmitter and receiver in response to optimization signals generated within the implant and relayed back to the transmitter. Details are discussed below in connection with the relevant figures. The ultrasound receiver is contained within an implantable case, the external surface of which is biocompatible material. It may be implanted at a functionally appropriate distance below the skin surface, e.g. typically about 10 mm to about 50 mm below the skin surface, or some distance larger, between, or smaller than those distances. The front, flat face of the implant is fixed in the tissue approximately parallel to the front, flat face of the transmitter. Experiments with curved transducer faces, such as used for focusing, showed poor efficiency because of the sensitivity of the curved transmitter and receiver faces to misalignment. Within the implant case are components for wireless radio frequency communication with the external controller, electronics for converting the ultrasound to electrical power, methods for monitoring the output power, sensors for monitoring the temperature at various points within the implant, sensors for monitoring and obtaining the optimum conversion efficiency, and output devices to 1) an implanted battery and 2) directly to the implanted MCSS.

There are two geometrical issues affecting alignment of a transmitter over a receiver in both the electromagnetic and ultrasound methods. The first is lateral translation over the implant, and the second is angular misalignment between the transmitter and receiver. With ultrasound, the use of an array transmitter enables compensation for both of these misalignments. The power out of the receiver, or a quantity proportional to the power such as voltage or current, is a signal fed back to the external controller which initiates the algorithm directing the array transmitter to search for the optimum alignment. In another embodiment, an imaging ultrasound system is added to the transmitter unit to provide the feedback on the depth and orientation of the implanted receiver, thereby assisting alignment. In another embodiment, some elements on the periphery of the array can be selectively energized to reflect ultrasound signals off the nearby receiver, either continuously or in pulse-echo mode. This will provide separation information in at least four quadrants, which is then used to correct for misalignment. While such signals have been used before, they have not been a simple by-product of having an initial 2-D array, hence their employment in this case does not require additional parts. Details are discussed below in connection with the relevant figures.

The present invention in one aspect provides a bio-implantable energy capture and storage assembly, for implantation into tissue comprising:
  i. an acoustic energy transmitter and an acoustic energy receiver, the acoustic energy receiver also functioning as an energy converter for converting acoustic energy to electrical energy at a rate of at least 5 Watts;
  ii. an electrical energy storage device electrically connected to the energy converter, wherein the acoustic energy receiver-converter is contained within the device for implantation in tissue;
  iii. an acoustic energy transmitter external to the body and separate from the implant, and wherein the transmitter comprises at least one transducer comprising a 2-dimensional array of elements arranged in a substantially regular 2-dimensional geometric shape on a support; and
  iv. a cooling system including a circulating coolant and heat exchanger for removing heat from the energy transmitter, tissue, and implant at a rate of at least 3 Watts; wherein the transmitter operates at a frequency in the range of 0.75 to 1.5 MHz.

In one embodiment the transmitter is comprised of a 2-dimensional array of elements arranged on a support, preferably selected from the group consisting of a circle, a rectangle, a square, a pentagon, a hexagon and an octagon.

In another embodiment, the bio-implantable energy capture and storage assembly includes a wireless feedback loop between the implant and transmitter used to optimize or stabilize the output power, with an algorithm using successively smaller scanning steps for monitoring one or more parameters related to an output power of the receiver.

In one embodiment the transmitter operates at a frequency of 0.9 to 1.1 MHz

In yet another embodiment, the bio-implantable energy capture and storage includes a heat-pipe device for cooling the energy transmitter, the tissue and the implant, and may also further include sensor transmitters and receivers on the acoustic energy transmitter, connected in said feedback loop. In such case, the sensor transmitters and receivers preferably may comprise ultrasonic elements.

In still yet another embodiment, the transmitter is comprised of a 2-dimensional array of elements arranged on a support, wherein the 2-dimensional array performs lateral alignment by electronically determining the minimum number of elements to be powered resulting in maximum power delivery to the energy converter within the receiver, or the 2-dimensional array performs angular alignment by electronically scanning the ultrasound beam over the face of the receiver determining the beam angle at which the power delivery is maximized to the energy converter in the receiver.

In another embodiment of the invention the transmitter is comprised of a 2-dimensional array of elements arranged on a support, wherein the 2-dimensional array relaxes the criteria on angular alignment by substituting the width of an array element for the width of the entire array, thus relaxing the criteria for angular alignment.

The present invention also provides a bio-implantable energy capture and storage assembly for implantation into tissue of a body of a living animal, comprising:

i. an acoustic energy transmitter and an acoustic energy receiver, the acoustic energy receiver also functioning as an energy converter for converting acoustic energy to electrical energy at a rate of at least 5 Watts;
ii. an electrical energy storage device electrically connected to the energy converter, wherein the acoustic energy receiver-converter is contained within the device for implantation in said tissue;
iii. an acoustic energy transmitter external to the body and separate from the implant, and wherein the transmitter comprises at least one transducer comprising a 2-dimensional array of elements arranged in a substantially regular 2-dimensional geometric shape on a support;
iv. a cooling system including a circulating coolant and heat exchanger for removing heat from the energy transmitter, tissue, and implant at a rate of at least 3 Watts; wherein said transmitter operates at a frequency in the range of 0.75 to 1.5 MHz, and
v. a device for providing conditioned power directly to a load, connected to said energy converter, wherein the acoustic energy receiver-converter is contained within a biocompatible implant for implantation in tissue, wherein said acoustic energy transmitter is separate from said implant.

In one embodiment the transmitter is comprised of a 2-dimensional array of elements arranged on a support, preferably selected from the group consisting of a circle, a rectangle, a square, a pentagon, a hexagon and an octagon In another embodiment, the bio-implantable energy capture and storage further includes a wireless feedback loop between the implant and transmitter used to optimize or stabilize the output power, with an algorithm using successively smaller scanning steps for monitoring one or more parameters related to an output power of the receiver.

In one embodiment, the transmitter operates at a frequency of 0.9 to 1.1 MHz.

In another embodiment the bio-implantable energy capture and storage assembly further includes a heat-pipe device for cooling the energy transmitter, the tissue and the implant and may also further include sensor transmitters and receivers on the acoustic energy transmitter, connected in said feedback loop. In such case, the sensor transmitters and receivers preferably may comprise ultrasonic elements.

In one embodiment of the invention, the transmitter is comprised of a 2-dimensional array of elements arranged on a support, wherein the 2-dimensional array performs lateral alignment by electronically determining the minimum number of elements to be powered resulting in maximum power delivery to the energy converter within the receiver, or the 2-dimensional array performs angular alignment by electronically scanning the ultrasound beam over the face of the receiver determining the beam angle at which the power delivery is maximized to the energy converter in the receiver.

In yet another embodiment of the invention, the transmitter is comprised of a 2-dimensional array of elements arranged on a support, wherein the 2-dimensional array relaxes the criteria on angular alignment by substituting the width of an array element for the width of the entire array, thus relaxing the criteria for angular alignment.

BRIEF DESCRIPTION OF THE DRAWINGS

Further features and advantages of the present invention will be seen from the following detailed description, taken in connection with the following detailed description, wherein like numerals depict like parts, and wherein:

FIG. 2B is a block diagram of the components contained within the transmitter assembly part of the invention;
FIG. 3B shows the possible arrangement of the controller, transmitter, receiver and batteries on the body of a patient, frontal and side views;
FIG. 6 show lateral alignment of an array transmitter and receiver in accordance with the present invention;
FIGS. 6A-6D show other geometric arrangements for lateral alignment of an array transmitter.

DETAILED DESCRIPTION

Overall Assembly

Figure 1:
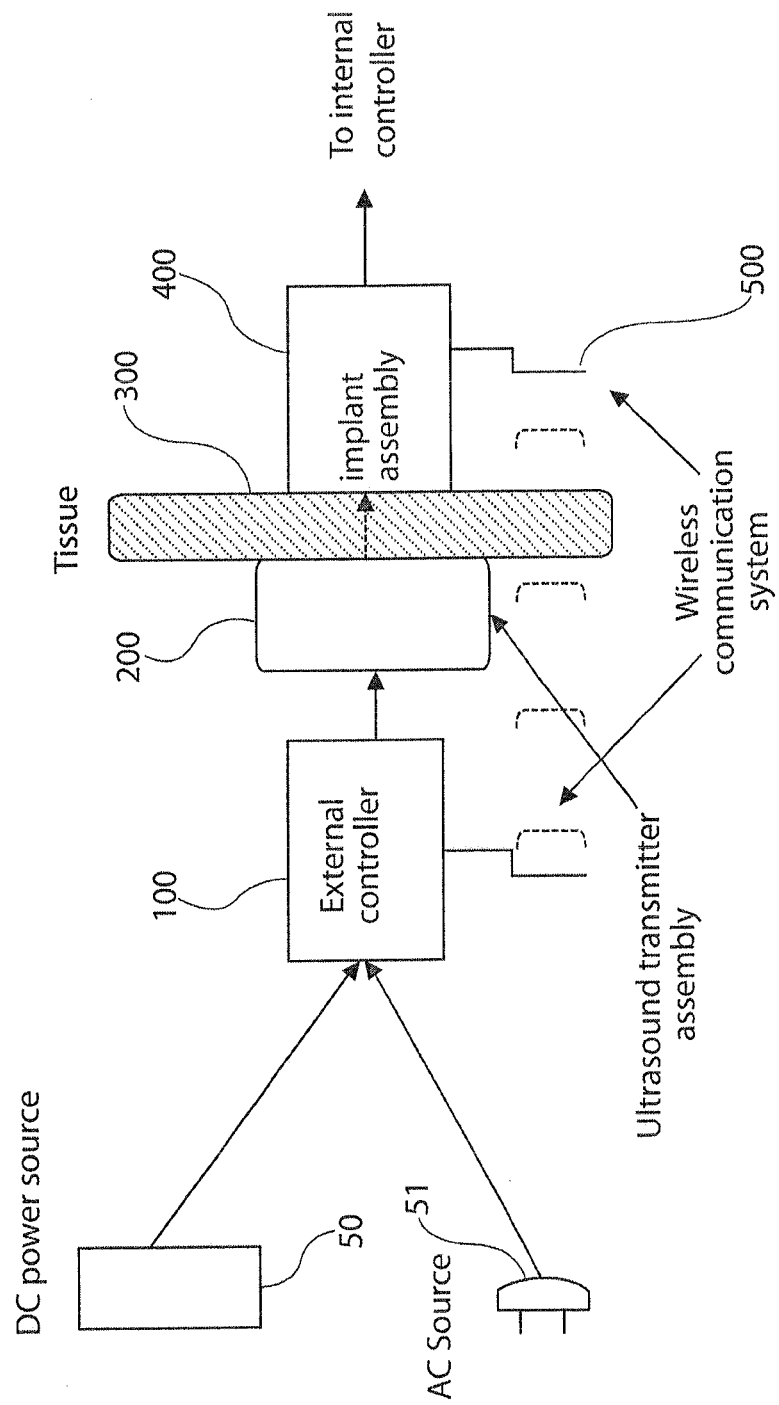
FIG. 1 is a schematic of the system of the present invention.
Figure 2A:
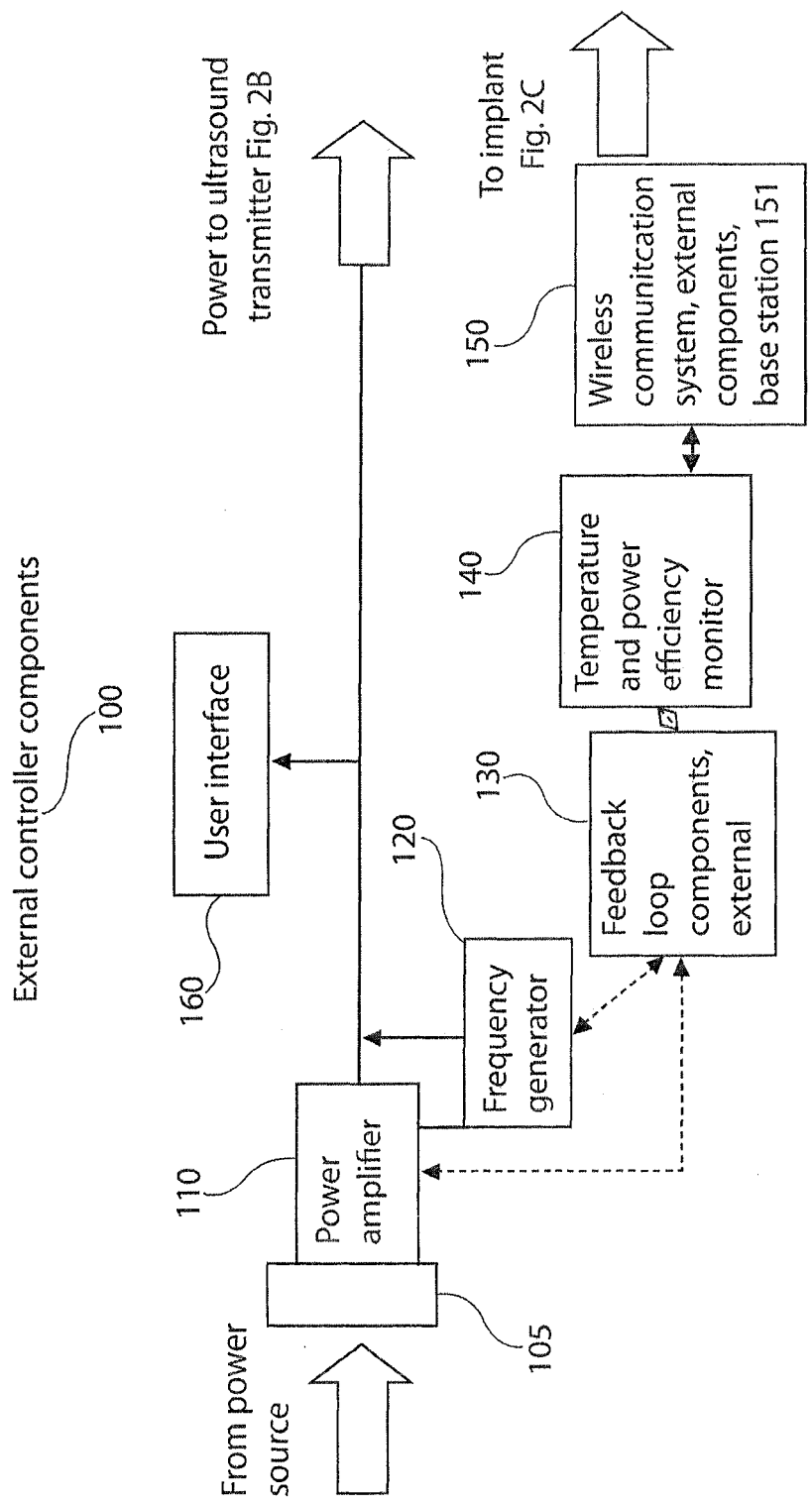
FIG. 2A is a block diagram of the components contained within the external controller part of the invention, including non-mechanical alignment, coupling, and cooling.
Figure 2C:
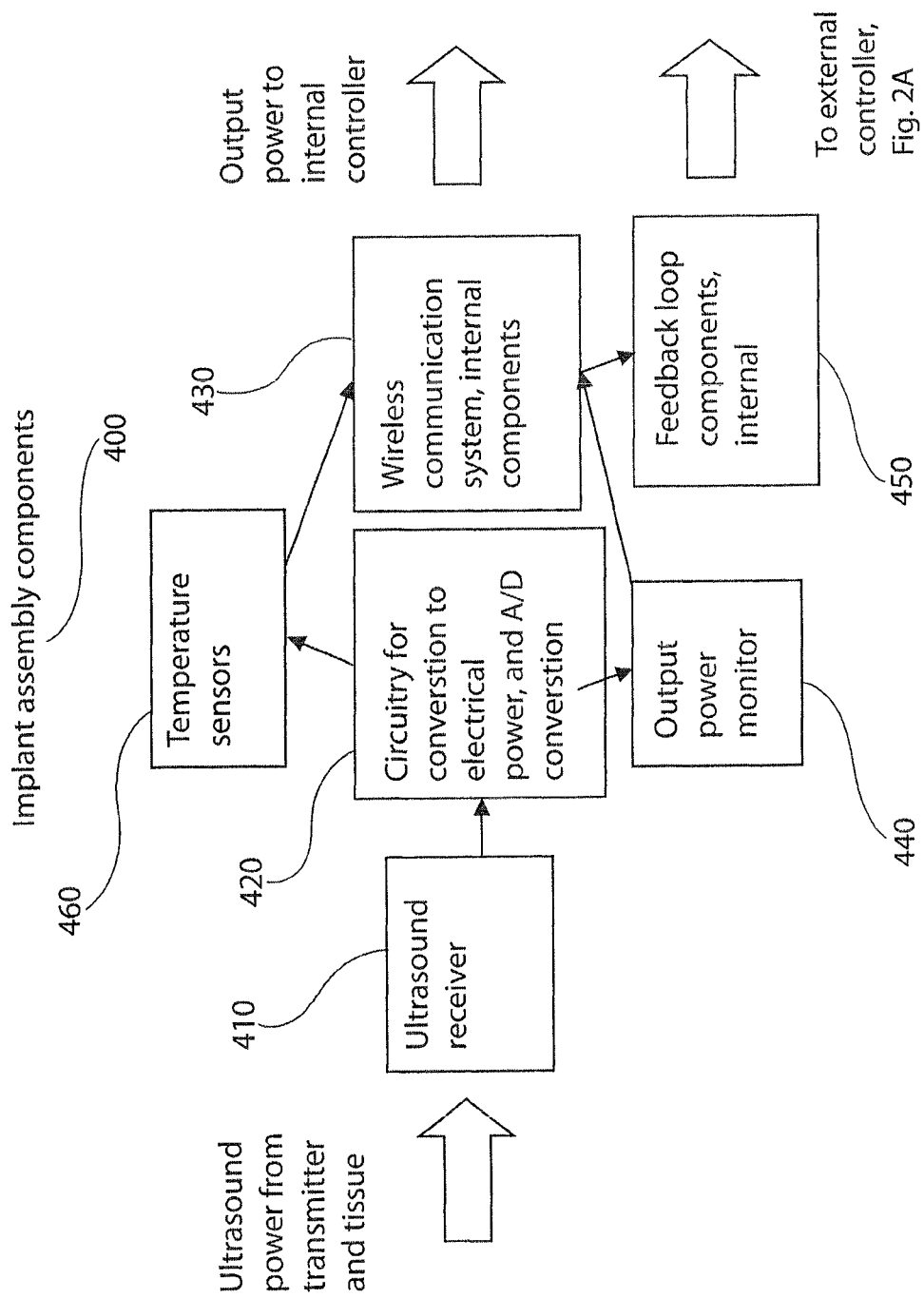
FIG. 2C is a block diagram of the components contained within the implant assembly part of the invention.

FIG. 1 is an overall block diagram of an US-TET system in accordance with the present invention. FIGS. 2A, 2B, and 2C are block diagrams the items within the external controller 100, the transmitter assembly 200, and the implant assembly 400 and are discussed in later sections. Referring to FIG. 1, two possible sources of power can operate the system. They are either a direct current (DC) power supply 50 such as a battery, typically worn by the patient, or a conventional room alternating current (AC) source 51. Circuitry within the external controller 100 determines whether the input power is low frequency AC. If so, it proceeds through a DC converter and then through circuitry 120 which converts it to high frequency ultrasound. The external controller 100 controls the level of input power, frequency of the ultrasound, alignment algorithm, and cooling level. These can be operated in two modes, manually and automatically, the latter via a feedback loop 130 and 450 made possible by the wireless communication system 500, which has external 150 and internal 430 components. The output of the external controller 100 is connected to the transmitting assembly 210, which is disposed adjacent to the skin of the subject. After transmission through human tissue 300 the ultrasound is incident on the receiver 410, which is disposed on or under the face of the implant 400 adjacent to internal tissue.

After conversion back to electrical power via circuitry 420 residing within the implant 400, the power is directed to an implanted controller which modulates the current and other sensors for the operation of the MCSS, and as necessary, to replenish an internal DC source such as a battery. The internal battery is used to power the MCSS for short periods of time such as a few hours, while the patient removes the external supply to bathe or for other conveniences. A radio frequency wireless communication system 500 between the external controller and the implant, such as a Zarlink or other brand over the 405 MHz medical-band system, provides a means of monitoring functions of the receiver and implant, issuing performance commands to the elements within it, and maintaining one or more feedback loops 130 and 450 for optimization of performance.

Figure 3A:
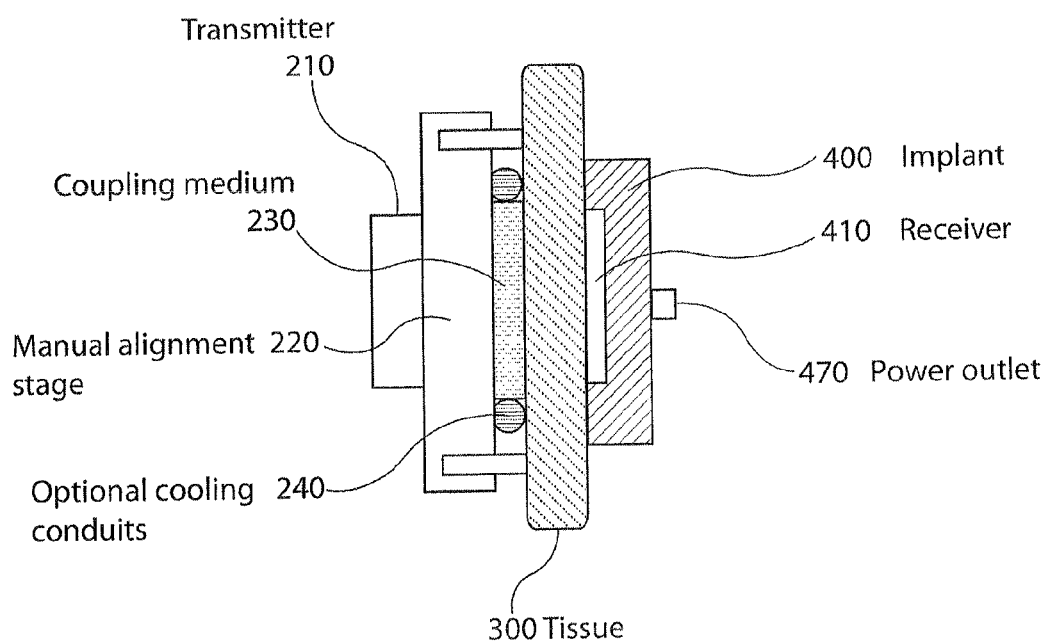
FIG. 3A is a schematic of the transmitter, tissue, and receiver part of the system of the invention.

FIG. 3A shows a schematic arrangement of the transmitter-tissue-implant part of an US-TET system. The transmitter transducer 210 transmits acoustic energy which is continuous, via sine waves, square waves, triangular waves or an arbitrary repetitive shape. Continuous power in this context is as opposed to pulsed power, and does not exclude occasional periods of no power delivery for whatever reason, during which the internally charged batteries take over the operation of the MCSS. The power is transmitted wirelessly through an external acoustic-coupling medium between transmitter and tissue 230. Occasional quasi-continuous operation simultaneous with or separate from continuous operation, may be necessary for alignment or other reasons. Essentially all air preferably will be excluded, between the skin of the patient and the ultrasound transmitter, since air strongly attenuates ultrasound over frequencies of 100 kHz. A cooling system 240, is deployed as schematically shown. During in vivo tests external cooling has been observed to penetrate the dermis, cooling the intervening tissue and the implant as well. After penetrating the epidermis, dermis, and possibly fat and muscle layers, the ultrasound is incident on a biocompatible implanted container 400 which has the receiver 410 on or against the inside of the front face, and other elements packaged within it. The receiver transducer 410 converts the acoustic to electrical energy. This energy proceeds via the schematically shown power outlet 470, which leads to the internal controller, power conditioning circuitry, and then to an application such as the MCSS.

FIG. 3B shows how the transmitter, receiver, batteries and controller may be positioned on a person to deliver power to an MCSS. In the side view, the transmitter unit 210, with input from the controller 100, transmits the ultrasound through the intervening tissue to the receiver unit 400. Those units may be placed in any location on the body, anterior or posterior, found to be advantageous. In a preferred embodiment the transmitter and receiver would be above and near the heart for MCSS applications, so that wires inside the body can be kept short. The front view shows the straps as in the present EM-TET method. The external batteries 310 are attached to the straps, and can be easily removed and replaced with fresh batteries as needed. Depicted also is the connection between the receiver 400 and an MCSS device 320 which assists the heart in its operation.

Transmitter and Receiver Ultrasound Transducers

Figure 4:
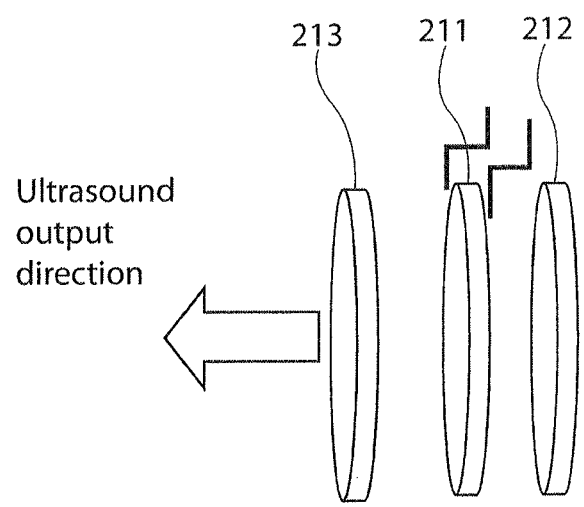
FIG. 4 shows the typical parts of an ultrasound transducer.

An ultrasound transducer is a device which converts electrical energy to vibrational energy, and vibrational energy to electrical energy useful in the present invention. In its simplest form (FIG. 4) it is comprised of a piezoelectric material which changes its dimensions when an electric field is placed across it. These include ceramic, crystalline, composite and polymer piezoelectrics. Other materials may be used, such as magnetostrictive materials or CMUTs. In one embodiment, a piezoelectric disk 211 comprised of a ceramic matrix in which are embedded crystals of Lead-Zirconium-Titanate (PZT) can be the basis of a transducer. Other materials such as crystalline Lead-Magnesium-Niobate in Lead-Titanate (PMN-PT) may also be used. In general the ultrasound transducer may be a single element, or an array of individual elements. The piezoelectric surfaces are coated with a conducting film to which electrodes are attached and which carry the electromagnetic wave to the material, causing it to shrink or expand slightly at the frequency of the wave. The disk normally has a backing to augment the conversion, and is housed in a case made of plastic or aluminum or titanium or other material. In the implant, the disk and an impedance matching layer are preferably bonded directly to the inner face of a titanium implant case 400 which contains all the components of the implanted device, and which is hermetically sealed. The element between the disk and the medium through which the vibrations are passing has a thickness such as to minimize the reflection of the wave, typically a quarter or full wave thick, and possibly comprised of multiple layers.

The transmitter 210 and receiver 410 transducers may have a high-Q (narrow bandwidth) and be designed and manufactured to have closely matched resonance frequencies. In a second embodiment, one of the units may have a high-Q resonant frequency and the other a lower-Q wider bandwidth resonance, making the combination less sensitive to temperature-induced changes of frequency in either unit. In a third embodiment, both units may have a lower-Q and wider bandwidth. It is well known to those skilled in the art that maximum electrical or acoustic power is transferred between two objects when their electrical and acoustical impedances are matched (Woodcock, 1979). Optimization of the transducer impedances is assisted by impedance matching software and accomplished with the addition of inductive and capacitive elements in the transmitter and/or receiver circuits.

Figure 5:
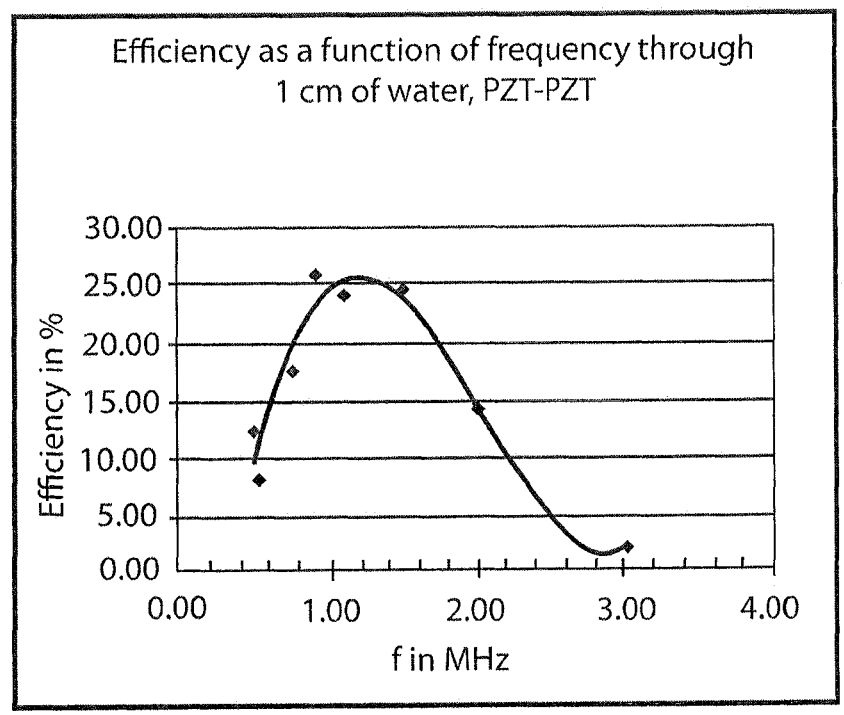
FIG. 5 illustrates the efficiency of ultrasound power transmission as a function of frequency in accordance with the present invention.

The operating frequency of the transducers is determined by a variety of constraints. At too low a frequency, below 500 kHz, there is the increased probability of cavitation which can lead to embolisms. At higher frequencies above 1 MHz, the absorption of tissue increases considerably, and the transducer element becomes quite thin. A series of experiments whose results are shown in FIG. 5 determined that an optimum frequency is in the range of 0.75 to 1.5 MHz. A narrower band of approximately 200 kHz centered on 1 MHz is an adequate working range within the wider band, allowing slight changes in operating frequency with changes in temperature. In addition to the resonant frequency, the bandwidth is also an important transducer parameter. Too small a bandwidth, such as in the kilohertz range, can lead to a lack of overlap of the transmitter and receiver resonant frequencies due to differential heating of transmitter and receiver during operation, with a consequent loss of transmission efficiency. This is an important tradeoff, central for efficient operation at a constant power level.

Design of Safe High-Power Transmitter and Receiver Transducers

A primary consideration in wireless transmission of power through tissue, whether it be electromagnetic or ultrasound, is the avoidance of tissue damage. There are well known guidelines to achieve this for pulsed ultrasound applied to fetal tissue, keeping the acoustic intensity at the skin at or below a maximum of 0.7 W/cm$^2$ (AIUM, 1993; Hedrick, 2005; NCRP Report 113, 1992). This is a very conservative value adopted to avoid significant temperature rise in critical tissue structures in the fetus during pulsed obstetrical imaging. Adoption of this metric for our continuous power delivery, dictates, for a given input electrical power, the minimum area of a transmitter that applies the power to a patient.

An example calculation of a sufficiently large transducer area follows. Assume a conversion efficiency of electrical to ultrasound power of 70%. Then 1 W/cm$^2$ electrical intensity would produce 0.7 W/cm$^2$ of acoustic intensity. In passage through one cm of tissue at 1 MHz about 20% of the acoustic energy would be absorbed. The efficiency reconversion to electrical energy at the receiver is assumed be the same, 70%. The total efficiency then is 40%. In the experimental table shown in the section on cooling below (Table 2), efficiencies at high powers measured in proof of principle experiments averaged 30%. Likely sources of other losses are reflection from interfaces between different tissue layers and between tissue and the solid surfaces of the transducers. Assume that 20 Watts of electrical power is necessary to operate the MCSS. That places a requirement of just under 70 Watts of electrical power at the transmitter, 50 Watts acoustic power. This requires a transmitter area of 70 cm$^2$ (diameter of 9.5 cm) to keep the acoustic intensity at 0.7 W/cm$^2$. An additional metric for device safety is that tissue temperature increase due to the TET system application be less than 2° C. That metric is met by having sufficient cooling capacity. Another safety concern is mechanical particle motion. Using conventional expressions for the relationship between ultrasound intensity and particle motion in water (analogous to soft tissue), at 0.7 W/cm$^2$, particle motion is calculated to be a very small amount.

The main non-thermal possibility for tissue damage arises from cavitation, rapid expansion and contraction of air bubbles, primarily in the lungs. The probability for this effect increases with ultrasound frequencies below 500 kHZ, and for locations where ultrasound can interact with lung tissue. Avoiding such locations and using a frequency around 1 MHz minimizes this possibility.

External Controller

As shown in FIG. 2A, the external controller 100 contains a variety of components. When converting from input DC power, it goes through a DC to DC converter 105 to bring it to a range of useful current and voltage. It then proceeds to a signal generator 120 such as a variable frequency oscillator or a synthesized signal generator to condition it to the frequency of interest. When converting from input alternating current, which may be 120 V, 60 cycle or some other normally used combination, first the electrical power goes through an AC to DC conversion 105, and then follows the steps outlined above for a DC power source. In both cases the power at the appropriate ultrasound frequency then proceeds through an amplifier 110 to bring it to the level required for the application. The power level can be set manually by an input command, or be placed under the control of a feedback loop 130 and 450 which keeps it at the specified value. A useful feedback parameter, whose value is relayed from the implant to the external controller, is the output power from the ultrasound receiver. Typically it would be desirable to keep the output power stable for optimum operation of the application.

A second important function of the controller is to monitor and change the frequency of the ultrasound. Typically the range of changes are approximately 10% of the resonant frequency, and this is achieved via a variable frequency oscillator 120 or a synthesized signal generator 120, methods well known to those skilled in the art. The frequency can be set manually with an input command, or can be placed under the control of a frequency feedback loop 130 and 450.

Two other important functions are a) monitoring and aligning the transmitter and receiver faces non-mechanically, b) controlling the cooling mechanism to regulate the heat removal needed for safe operation.

Embedded in the controller is the radio frequency antenna 150 which enables reception of communications from the implant on a medical communication band. These include receiving values of temperatures 140 being monitored in various implant locations, monitoring the efficiency of power conversion 140, and monitoring transmitter and receiver unit alignment. In one embodiment, a hybrid National Instruments Signal Express plus C++ code collects and stores the data automatically and continuously for up to 10 parameters, both for patient information on a user interface 160 and for periodic diagnostic downloading. The latter allows a variety of charts, comparisons, and figures of merit to be recorded and analyzed, to monitor the performance of the system.

Software compares the temperature readings with a preset regime of safe temperatures and, if necessary, sends a warning to a user interface 160, similar to a smart phone, which allows the patient to monitor power efficiency and receive safety warnings. The user interface communicates with the controller using a wireless protocol, such as Bluetooth, Wi-Fi, or other advanced method.

Transmitter Unit and Components

As shown in FIG. 2B, power from the external controller 100, at an ultrasound frequency, proceeds to the transmitter assembly 200 and transmitter transducer 210. The transmitter transducer is preferably a two dimensional array of elements. This activates the transmitter transducer 210 to convert electrical power to ultrasound for transmission through human tissue 300. The transmitter alignment stage 220 contains a method of being fixed to the patient, a manual adjustment method to approximately align the transmitter and receiver faces, a non-mechanical adjustment algorithm and electronics to complete the alignment of the wave front from the transmitter parallel to the receiver face, a space for an element 230 which excludes air between the ultrasound transmitter and the skin of the patient, and a cooling method 240. The alignment stage may be fixed to the skin by means of a double sticky tape on the bottom or over the top of the alignment stage (Mehta et al., 2001, FIG. 3). Another embodiment has a strap or holster in addition to or in place of the sticky tape to secure the transmitter unit to the skin. Another embodiment attaches the stage via a slight suction generated by a boot and clamp method, as used for affixing items to the inside of an automobile windshield. The manual adjustment method, in one embodiment, is comprised of a platform with three screws of fine pitch set in a triangle, which aligns the platform angularly over the implant. Initial lateral alignment is performed over the slight protrusion of the implant which rises from a few millimeters to one centimeter or more over the adjacent tissue. A lightweight cone on the bottom of the alignment platform may fit over the protrusion, ensuring secure lateral alignment.

Implant Unit and Components

FIG. 2C is a block diagram of the components of the implant assembly. FIG. 3 illustrates the placement of the implant 400 connected to the tissue 300. The piezoelectric element 410 which is the key element of the receiver transducer, is placed on the front face of the implant 400, or underneath it and permanently affixed to it. Preferably it is a single element transducer, although an array may be used in another embodiment. Adjacent to that element is found circuitry 420 which converts the ultrasound to electrical power, AC or DC, as required by the application which is receiving the power. The converted power is monitored 440 and the analog data stored. Embedded in various locations in the implant will be thermal sensors 460 which enable the temperatures in those locations to be monitored. Circuitry for analog to digital conversion of those data 420 are also embedded in the implant, as are internal radio frequency wireless communication components 430, including an antenna. The data so transmitted are the input for the feedback loop 130 and 450. The external controller 100 then resets parameters such as power, frequency, and alignment in order to stabilize the power provided to the internal application.

Non-Mechanical Alignment of Transmitter and Receiver

Alignment of the transmitter and receiver is an important issue both in EM-TET and US-TET. Even though the transmitter unit may be affixed securely to the skin over the implant, it is possible that the implant could move slightly within the somewhat flexible tissue in which it is placed. Motion of the patient will affect the alignment as well. Hence a method of both lateral translations and angular alignment in the post-implanting phase, is desirable and necessary. Furthermore, it is desirable that the methods of alignment not depend on the patient's intervention, because the system will be required to operate even when the patient is asleep. Ultrasound provides a method for non-mechanical alignment not available to EM-TET.

One dimensional arrays of ultrasound transmitter elements are well known to those skilled in the art. Their principal applications are for scanning an ultrasound beam in space to image structures in the body, and for non-destructive testing of materials and weld integrities. Two dimensional arrays have been made as well, and the technology is advancing to make inexpensive 2-D arrays (Ranganathan, et al., 2004; Fuller et al., 2009). Willis (US2008/0294208) has used a two dimensional array to locate a deeply embedded receiver and to focus very weak ultrasound energy on it to provide pacing signals to the heart.

FIG. 6 shows an arrangement for lateral alignment of a larger circular 2-D array 215 over a smaller circular receiver 410. Preferably the 2-D array of the transmitters is arranged on a circular disk, e.g. as shown in FIG. 6, although other regular 2-D geometric arrangements, e.g. square, pentagonal, hexagonal, octagonal, etc., shapes may be used as illustrated in FIGS. 6A-6D. In the algorithm for lateral alignment, a feedback loop 130 and 450 relays the output power level of the receiver back to the controller 100 that activates a number of elements in the 2-D array transmitter 215. The controller 100 activates elements sequentially along one axis, and then along a second axis perpendicular to the original direction. In this way the centroid of the active elements that maximizes or optimizes the output power is obtained. Once the optimum centroid position is determined, the number of array elements surrounding that point is increased radially until the output power plateaus, thus minimizing waster energy. That array of elements remains activated until a significant departure from the chosen output power is observed with the feedback loop 130 and 450, leading to a rescanning. The frequency of rescanning depends on the rapidity of changes in the lateral position, which is likely to be slow.

Figure 7A:
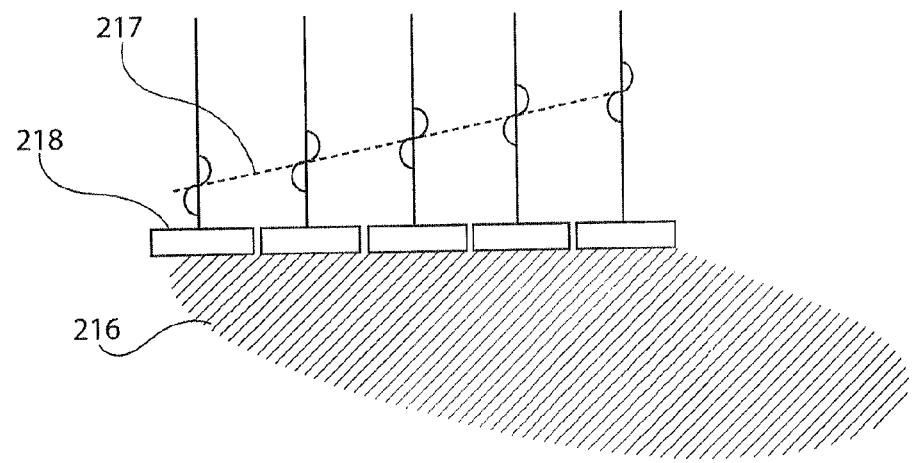
FIG. 7A illustrates ultrasound beam turning using an array of transmitters with a phase difference imposed between the elements of the array in accordance with the present invention.

For angular alignment two effects are considered. The first of these is the turning of the beam wave front from parallel to the face of the transmitter array, through an angle that makes the wave front parallel to the face of the implanted receiver. This compensates for angular misalignment of the faces of the two transducers. For two dimensional surfaces this needs to be done along two axes. It is well known to those skilled in the art that this is accomplished by embedding a constant time differential, which results in a phase difference, between each element of the array. The result is shown schematically in FIG. 7A which illustrates the beam turning 216 by introducing a constant phase 217 between elements of a one-dimensional array 218.

Figure 7B:
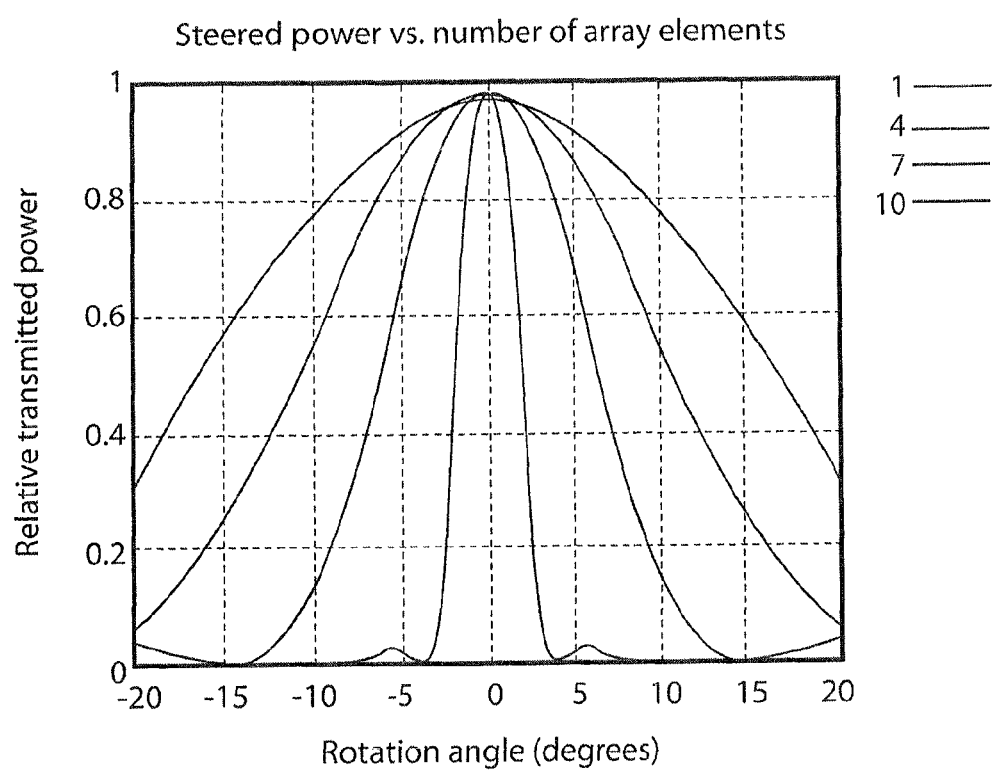
FIG. 7B illustrates the desensitization of power delivery to angular misalignment as the number of elements in a linear array increases, for transducers of 25 mm diameter and a frequency of 1 MHz in accordance with the present invention. The narrowest trace corresponds to one element, the broadest to ten elements.
Figure 7C:
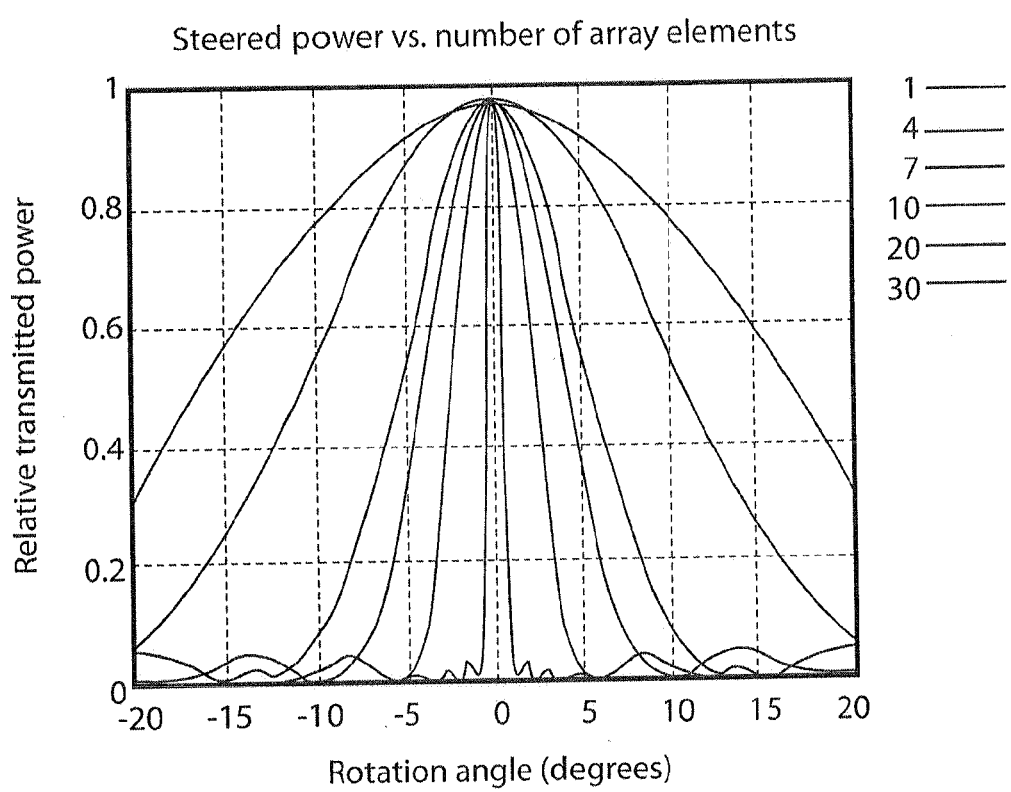
FIG. 7C illustrates the desensitization of power delivery to angular misalignment as the number of elements in a linear array increases, for transducers of 75 mm diameter and a frequency of 1 MHz in accordance with the present invention. The narrowest trace corresponds to one element, the broadest to thirty elements.

The second effect deals with decreasing the sensitivity to alignment of two plane parallel transducers faces. Maximum power transfer takes place when the incoming wave is at the same phase at all points on the receiver. In order to keep the incoming wave from the transmitter in phase across the face of the receiver, the two must be aligned to within one-half wavelength. For a frequency of one MHz in tissue that is approximately 1 mm. This alignment condition becomes more and more stringent as the diameter of the transducers increase. For a 10 mm diameter transducer, the alignment condition is that the two surfaces be parallel to 1 mm out of 10 mm. For a 70 mm diameter transducer, the condition is 1 mm out of 70 mm. This condition is relaxed for an array because the width of the array element substitutes for the overall width of the whole array. An array element width can vary from 0.1 mm to several millimeters. This relaxation is shown in FIG. 7B in a model-based calculation result for an ultrasound frequency of 1 MHz. There is plotted the steered power versus the number of array elements for a pair of 25 mm diameter transducers, where the transmitter is a one-dimensional array, and the receiver a monolithic single element. The narrowest trace is for one element, then follow in increasing width the traces for 2, 3, and 4 elements. For a single 25 mm diameter transmitter element (the whole transducer), the power falls to 80% within a degree of misalignment on either side of the center line. Increasing the number of elements per unit area to 10 spreads the 80% power cone to +8°. That in turn, reduces the restriction on the angular alignment to retain 80% power, to +8°. FIG. 7C shows the result of a calculation for a 70 mm diameter transmitter array with up to 30 elements, and a monolithic 70 mm diameter receiver. The narrowest trace is for one element, then follow in increasing width the traces for 2, 3, and in sequence up to 30 elements. With 30 elements, the 80% power level is retained to +10°. By combining the relaxation on alignment due to the array, with a feedback loop, in one embodiment based on monitoring the output power of the receiver, a non-mechanical means of aligning the transmitted wave with the receiver face has been achieved. This method can be used to maximize power, or to retain a constant power level which is slightly below the most efficient operation. Hence alignment becomes a method to retain a very tight tolerance on the output power. To be effective in operation, it is necessary to have an array in two orthogonal directions, able to compensate for angular displacement along each of two axes. In the algorithm for angular alignment, a feedback loop 130 and 450 relays the output power level of the receiver back to the controller 100 that inputs the phase change from element to element in the 2-D array transmitter 215. The controller 100 inputs a series of phase changes sequentially along one axis, and then along a second axis perpendicular to the original direction. In this way the two angles are determined that maximize or optimize the output power. The angles thus optimized remain activated until a significant departure from the chosen output power is observed with the feedback loop 130 and 450, leading to a rescanning.

The Feedback Loop

The feedback loop 130 and 450 is illustrated in FIG. 2A and FIG. 2C, connecting the external controller with the implant. The basic feedback algorithm used to optimize the position of each axis of the lateral and angular alignments, and the frequency from the signal generator, is this. First, the angular or lateral position for each axis or the frequency is swept across its entire range with a gross step between each position or frequency, while measuring the level of the receiver power. Next, the positions and frequency are again swept but across a smaller range centered around the best position or frequency from the previous sweeps, and at a smaller step size. The process is repeated until a very fine step size thus narrowing in on the optimal frequency or position. Individual power measurements may vary due to electronic noise effects. With gross steps, it is easy to measure distinct changes, but as the step size decreases, the noise floor quickly overcomes the differences in power created by a change in position or frequency. To get a finer step size and still be able to discern a clear change in power, an averaging of ten measurements is useful. In another embodiment, the averaged measurements were filtered for each location and frequency. From digital signal processing it is known that an ideal low pass filter in the frequency domain is a sine function in the time domain. More formally, given the filter $H(\omega)$ defined below for the frequency domain $$H(\omega) = \begin{cases} 1, & -\omega \leq \omega_c \leq \omega \\ 0, & \text{else} \end{cases},$$

the inverse discrete time/space Fourier transform h(n) of the $H(\omega)$ is equal to $$h(n) = \frac{\sin(\omega_c n)}{\pi n},$$

where h(n) is the impulse response of the filtering system. This particular function is known as the sine function. The output is equal to the convolution of the input with the impulse response. Since this filter is symmetric, convolution with this filter is equivalent to cross correlation. Thus, the filtered power at a particular location or frequency $n_0$ is $$y(n_0) = \sum_{k=N-n_0}^{N+n_0} x(k)h(k)$$

where N+1 is equally to the number of coefficients of the symmetric filter and x is the signal of measured powers. Such a filter implementation is clearly not ideal because of the finite filter length of the filter and the finite precision of the digital values; however, the power measurements are filtered only to identify a clear peak in the data. At a low angular cut off frequency of around 0.5 radians (determined empirically) most of the AC components of the power measurements are removed. By implementing this filter as part of the algorithm, an optimal position for each axis and an optimal frequency are obtained in which adjustments no longer yield perceivably higher powers.

Cooling

Figure 8:
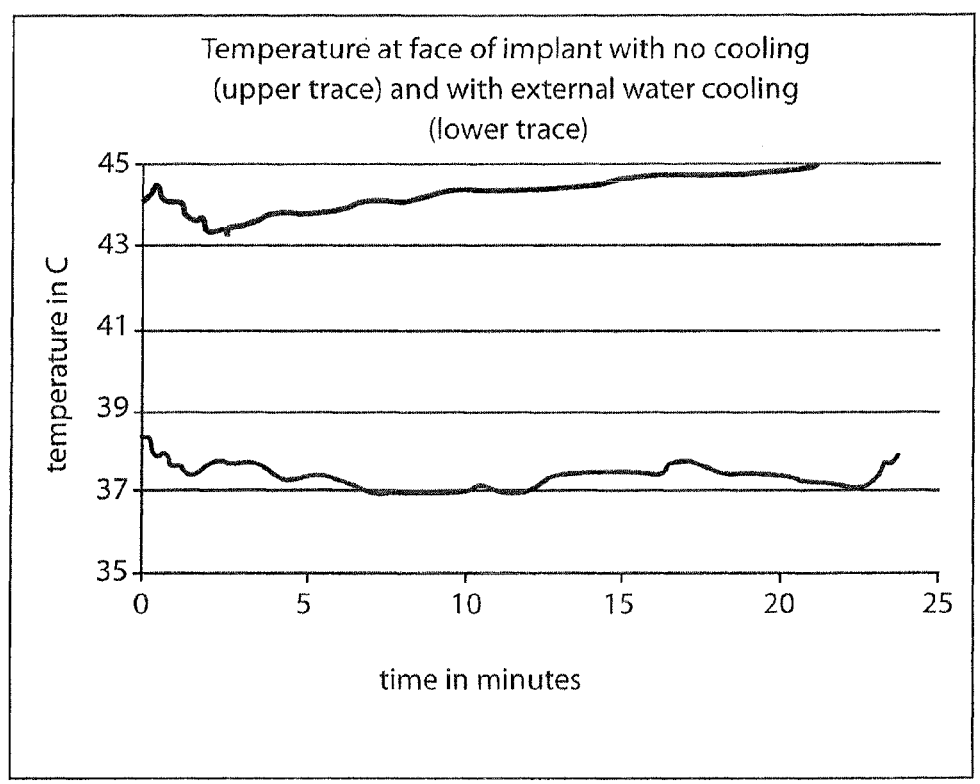
FIG. 8 illustrates the effect of cooling on the temperature at the face of the implant in accordance with the present invention.

A considerable amount of the input electrical power to the transmitter piezo element(s) is converted to heat because such elements are, as known in the art, at best typically 70% efficient in transduction from electrical to acoustic power. A cooling method will constrain tissue exposure to high temperature. Cooling was successfully accomplished in animal studies by circulating water through conduits around the base of the transmitter assembly as illustrated in FIG. 3, 240. The method provides cooling even through the intervening tissue to the bottom of the implant and the tissue adjacent to it, via conduction. This is illustrated in FIG. 8 which shows the temperatures measured in an in vivo porcine study, at the top of the implanted receiver, approximately 1 cm deep into the tissue, without (upper) and with (below) external water cooling, at ~120 mA of charging current into the implanted battery. With the water cooling the temperature of the tissue exposed was well controlled.

A calculation and experimental result will show the order of magnitude of the expected heat load. The Table 1 below shows an estimate of the power lost to heat in the two conversions and through 1 cm of tissue, with an input electrical power of 50 Watts. In this case the result is and efficiency of 40%, and 30 Watts lost to heat.

TABLE 1

A calculation of heating.

|  |  | lost to heat Watts |
|---|---|---|
| input electrical (Watts) | 50 |  |
| conversion efficiency (ratio) | 0.7 |  |
| resulting input acoustic power (Watts) | 35 | 15 |
| transmission of power through 1 cm of tissue at 1 MHz (ratio) | 0.8 |  |
| power remaining to receiver (Watts) | 28 | 7 |
| conversion efficiency (ratio) | 0.7 |  |
| electrical power out of receiver (Watts) | 19.6 | 8.4 |
| Total (Watts) |  | 30.4 |

To validate the estimates above, many experiments were performed with 3" diameter transducers, at input electrical powers of up to 60 Watts, through a 20 mm thick gel pad, while monitoring temperatures of transmitter and receiver faces with attached thermocouples. Data from one of these experiments in the Table 2 below illustrates the rapid increase in temperature without cooling. In 7 minutes the transmitter increased in temperature by 24 C, and the receiver 18 C. The overall efficiencies measured about 30%, somewhat lower than the 40% calculated. This was likely due to other losses such as reflections at interfaces.

TABLE 2

Experimental results on heating.

| Electrical Power in Watts | Temperature transmitter C. | Temperature receiver C. | time Hr:min | Electrical Power out Watts | efficiency % |
|---|---|---|---|---|---|
| 2 | 20.2 | 19.9 | 1:30 | 0.66 | 33 |
| 10 | 21.7 | 21.6 | 1:32 | 2.98 | 30 |
| 20 | 23.3 | 23.3 | 1:33 | 5.99 | 30 |
| 40 | 29.1 | 29 | 1:35 | 10.58 | 26 |
| 60 | 44 | 38 | 1:37 | 14.58 | 24 |

Desktop computer CPU coolers are available that are well-developed off-the-shelf units with 30 to 120 W cooling capacities that exceed the needs in MCSS applications demonstrated above. These systems are compact, efficient and relatively quiet in operation. The circulating pumps are capable of running continuously in computers for up to six years. (Kang et al. (2007)). The overall system in Kang et al. included a pump, cold plates, a heat exchanger and flexible tubing. Liquid cooling systems can incorporate single phase liquids, or 2-phase media such as used in heat-pipes. These thermal dissipation schemes are very feasible in actively cooling a heat source such as the ultrasound transmitter, either as a single element or, in a multi-element configuration.

In a preferred embodiment, the closed-loop liquid cooling system is attached to the proximal transducer surface or the housing. A heat dissipating blower fan and fin-array can be used in the ultrasound source embodiment, without or with the closed-loop liquid cooling system. In another embodiment, these systems are split and attached to one or more heat generating surfaces, such as ultrasound arrays. The current ultrasound MCSS embodiment with anticipated waste power specifications as calculated above can easily be accommodated in the design in order to achieve acceptable source temperatures of 35° C. or lower, over several years.

In another embodiment, the above combinations for thermal dissipation for closed loop circulation, circulating fans, and conductive fins are augmented by using a refrigerant based liquid/gas to achieve yet lower temperatures at the ultrasound source plane adjacent to the skin. This cold front plane propagates distally to further cool the exposed tissue as well as the receiver surface. In Kang et al., they show results from a heat-pipe based system. The input power generated by a CPU chip was approximately 20 W and the heat pipes maintained the temperature typically at 40° C. Without heat pipe operation, the temperature soared to 90° C. in less than 2 minutes.

The novelty of this approach to ultrasound cooling lies in adapting the CPU cooling methods to the MCSS application.

Wireless Radio Frequency Communication System

Figure 9:
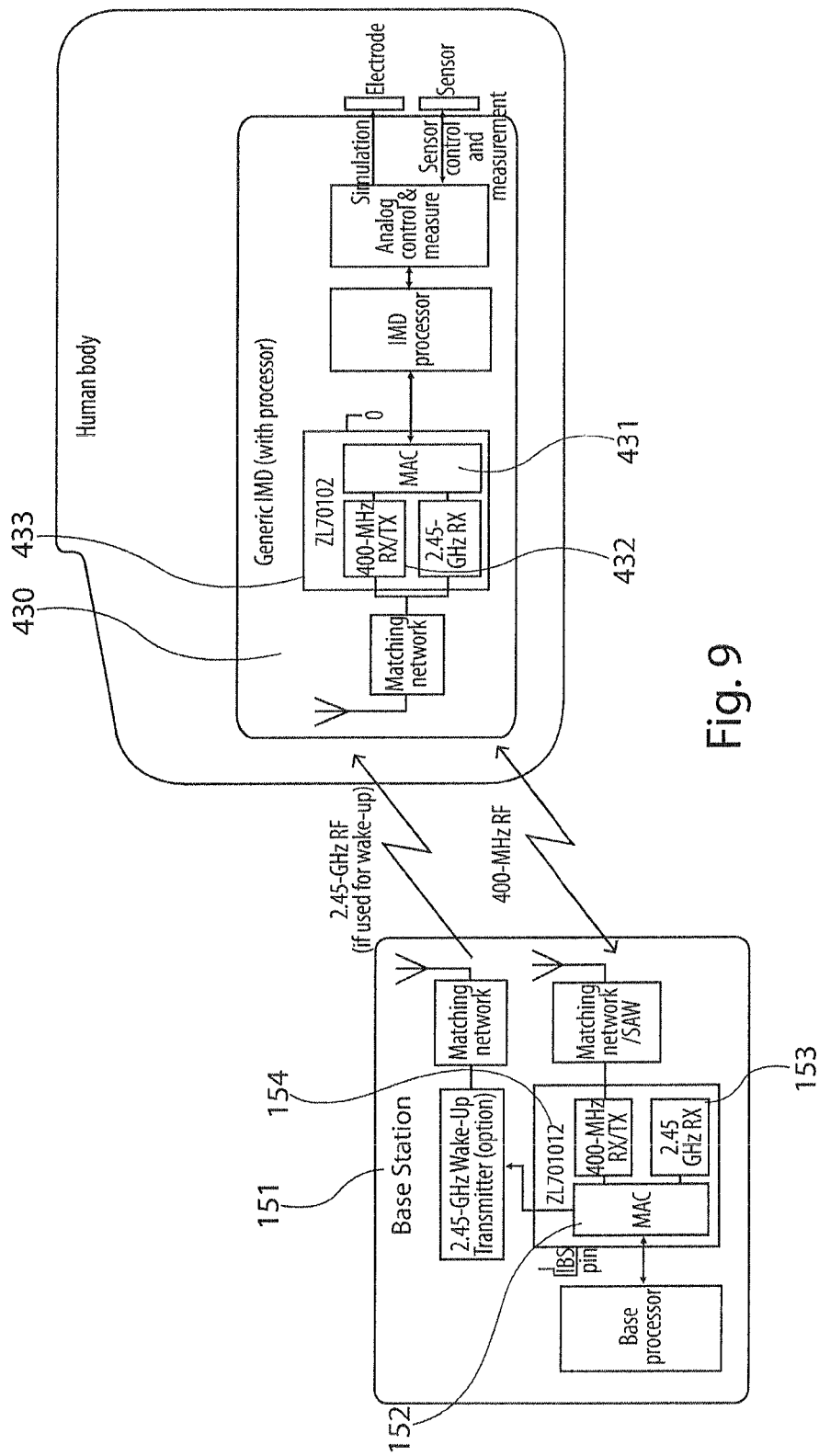
FIG. 9 is a schematic block diagram of the components of the wireless communication link in accordance with the present invention.

The purpose of an RF-Link is to have a wireless, bi-directional, non-invasive means of communication between a device implanted in a living human body, and an external controller. This provides the capability to remotely read out key parameters in the implant while permanently installed, and control parameters inside the implant, such as controlling a variable discharge dummy load to speed up battery discharging. FIG. 9 illustrates schematically the wireless communications RF-link 500 where an external base station 151 in an external controller 100 can communicate bi-directionally in half-duplex mode with the internal component 430 in the implant 400. The implant transceiver 430 device is paired with a microcontroller for added functionality. The base station 151 preferably is fitted with the microcontroller because sufficient power is always available. An example of a platform suitable for application to implants in humans, is Zarlink's medical implant communications service (MICS) band transceivers ZL70102. MICS is the industry standard for medical implants. It specifies low-power devices operating in the 400 MHz band without license requirement. Operating in the industrial, scientific and medical (ISM) band at 2.45 GHz is also license-free.

The system consists of a base station module 151, an implant module 430 and the required software package to control the system and communicate with the user interface. The hardware uses two microprocessors for the base station transceiver and two microprocessors for the implant transceiver. Zarlink provided the source code starting point, a software package that contains firmware for the microprocessors and an elaborate graphical user interface (GUI) that allows control of all features of the entire system from low-level bit addressing of registers to impedance-matching of the RF stages. The code is written in Visual C# and developed on the integrated development environment (IDE) Microsoft Visual Studio 2008.

The Zarlink chip uses a 2.45-GHz wake-up subsystem consisting of the 2.45-GHz receiver and the wake-up controller, plus an ultra-low-power, 25-kHz strobe oscillator that can be used for timing purposes. The wake-up controller is a digital subsystem that identifies when the implant module 430 receives a valid 2.45-GHz wake-up data packet from the base station 151, which is unique for a particular implant. The wake-up controller then powers up the media access controller (MAC) 431 and the 400-MHz transceiver 432, so that the implant can respond on 400 MHz and establish a two-way MICS-band link with the base station 151. While the 400-MHz link is operative, the 2.45-GHz wake-up subsystem is powered down. When the implant reverts to the sleep state, the 2.45-GHz wake-up subsystem is periodically re-enabled to listen for any possible wake-up transmissions.

In the base station 151, the MAC 152 provides a modulation signal for the external 2.45-GHz wake-up transmitter 153. The ZL70102 154 has features to facilitate and optimize a 400-MHz wake-up mode. A key feature of the ZL70102 is a fast received signal strength indicator (RSSI) sniff function that is optimized for sniffing and that leaves out operations that are required only for a normal wake-up. The bulk data communication takes place in the 400 MHz band while the wake-up calls are made in the 2.45 GHz band. The reason for the lower frequency for bulk communication is that 2.45 GHz electromagnetic waves experience significant absorption in body tissue, which is mainly water. With less loss at 400 MHz the transmitter power requirements are significantly less, an important feature for extending battery life.

When the implant 430 correctly receives the 2.45-GHz wake-up transmission from the base station 151, it responds using its 400-MHz transceiver 432. Therefore an on-chip, 2.45-GHz transmitter 152 is not needed. The base station 151 uses an external 2.45-GHz Wake-Up Transmitter module, which is controlled jointly by the application processor and the ZL70102 154. The wake-up function uses 2.45 GHz because the band is internationally designated as an ISM frequency band and so is more generally available on an international basis at a higher power level than other frequency ranges. The use of a higher transmitter power allows a reduction in the sensitivity of the wake-up receiver. Also, the use of a higher frequency tends to increase the received power available from the antenna, although this advantage is partly offset by the increased loss within the patient's body at 2.45 GHz. Taking all these factors into consideration, the overall result is a significant advantage in using 2.45 GHz. Zarlink recommends operation under the requirements for wideband data transmissions, as opposed to RFID regulations, since the allowable spectrum mask limits permit a faster rise time for the 2.45-GHz on/off keying. When operating under regulations for wideband data transmission, it may be necessary to provide frequency hopping in the 2.45-GHz transmitter 152. The bandwidth of the 2.45-GHz wake-up receiver in the ZL70102 433 is large enough that a substantial frequency spread can be used without loss of sensitivity caused by the mistuning of the input network.

The invention claimed is:

1. A bio-implantable energy capture and storage assembly, for implantation into tissue comprising:
   i. an acoustic energy transmitter and an acoustic energy receiver, said acoustic energy receiver also functioning as an energy converter for converting acoustic energy to electrical energy at a rate of at least 5 Watts;
   ii. an electrical energy storage device electrically connected to said energy converter, wherein said acoustic energy receiver-converter is contained within the device for implantation in said tissue;
   iii. an acoustic energy transmitter external to the body and separate from said implant, and wherein the transmitter comprises at least one transducer comprising a 2-dimensional array of elements arranged in a substantially regular 2-dimensional geometric shape on a support; and
   iv. a cooling system including a circulating coolant and heat exchanger for removing heat from the energy transmitter, tissue, and implant at a rate of at least 3 Watts; wherein said transmitter operates at a frequency in the range of 0.75 to 1.5 MHz.

2. The bio-implantable energy capture and storage assembly of claim 1, wherein said substantially regular 2-dimensional geometric shape is selected from the group consisting of a circle, a rectangle, a square, a pentagon, a hexagon and an octagon.

3. The bio-implantable energy capture and storage assembly of claim 1, further including a wireless feedback loop between said implant and transmitter used to optimize or stabilize the output power, with an algorithm using successively smaller scanning steps for monitoring one or more parameters related to an output power of the receiver.

4. The bio-implantable energy capture and storage assembly of claim 3, further including sensor transmitters and receivers on the acoustic energy transmitter, connected in said feedback loop.

5. The bio-implantable energy capture and storage assembly of claim 4, wherein said sensor transmitters and receivers comprise ultrasonic elements.

6. The bio-implantable energy capture and storage assembly of claim 3, wherein the 2-dimensional array performs lateral alignment by electronically determining the minimum number of elements to be powered resulting in maximum power delivery to the energy converter within the receiver.

7. The bio-implantable energy capture and storage assembly of claim 3, wherein the 2-dimensional array performs angular alignment by electronically scanning the ultrasound beam over the face of the receiver determining the beam angle at which the power delivery is maximized to the energy converter in the receiver.

8. The bio-implantable energy capture and storage assembly of claim 3, wherein the 2-dimensional array relaxes the criteria on angular alignment by substituting the width of an array element for the width of the entire array, thus relaxing the criteria for angular alignment.

9. The bio-implantable energy capture and storage assembly of claim 1, wherein the transmitter operates at a frequency of 0.9 to 1.1 MHz.

10. The bio-implantable energy capture and storage assembly of claim 1, further including a heat-pipe device for cooling the energy transmitter, the tissue and the implant.

11. A bio-implantable energy capture and storage assembly for implantation into tissue comprising:
   i. an acoustic energy transmitter and an acoustic energy receiver, said acoustic energy receiver also functioning as an energy converter for converting acoustic energy to electrical energy at a rate of at least 5 Watts;
   ii. an electrical energy storage device electrically connected to said energy converter, wherein said acoustic energy receiver-converter is contained within the device for implantation in said tissue;
   iii. an acoustic energy transmitter external to the body and separate from said implant, and wherein the transmitter comprises at least one transducer comprising a 2-dimensional array of elements arranged in a substantially regular 2-dimensional geometric shape on a support;
   iv. a cooling system including a circulating coolant and heat exchanger for removing heat from the energy transmitter, tissue, and implant at a rate of at least 3 Watts; wherein said transmitter operates at a frequency in the range of 0.75 to 1.5 MHz, and
   v. a device for providing conditioned power directly to a load, connected to said energy converter, wherein said acoustic energy receiver-converter is contained within a biocompatible implant for implantation in said tissue, wherein said acoustic energy transmitter is separate from said implant.

12. The bio-implantable energy capture and storage assembly of claim 11, wherein said substantially regular 2-dimensional geometric shape is selected from the group consisting of a circle, a rectangle, a square, a pentagon, a hexagon and an octagon.

13. The bio-implantable energy capture and storage assembly of claim 11, further including a wireless feedback loop between said implant and transmitter used to optimize or stabilize the output power, with an algorithm using successively smaller scanning steps for monitoring one or more parameters related to an output power of the receiver.

14. The bio-implantable energy capture and storage assembly of claim 13, further including sensor transmitters and receivers on the acoustic energy transmitter, connected in said feedback loop.

15. The bio-implantable energy capture and storage assembly of claim 14, wherein said sensor transmitters and receivers comprise ultrasonic elements.

16. The bio-implantable energy capture and storage assembly of claim 13, wherein the 2-dimensional array performs lateral alignment by electronically determining the minimum number of elements to be powered resulting in maximum power delivery to the energy converter within the receiver.

17. The bio-implantable energy capture and storage assembly of claim 13, wherein the 2-dimensional array performs angular alignment by electronically scanning the ultrasound beam over the face of the receiver determining the beam angle at which the power delivery is maximized to the energy converter in the receiver.

18. The bio-implantable energy capture and storage assembly of claim 13, wherein the 2-dimensional array relaxes the criteria on angular alignment by substituting the width of an array element for the width of the entire array, thus relaxing the criteria for angular alignment.

19. The bio-implantable energy capture and storage assembly of claim 11, wherein the transmitter operates at a frequency of 0.9 to 1.1 MHz.

20. The bio-implantable energy capture and storage assembly of claim 11, further including a heat-pipe device for cooling the energy transmitter, the tissue and the implant.

* * * * *